United States Patent [19]

Sato

[11] Patent Number: 4,987,236
[45] Date of Patent: Jan. 22, 1991

[54] OPTICALLY ACTIVE ALCOHOLS AND PROCESS FOR PRODUCING THE SAME

[75] Inventor: Fumie Sato, Fujisawa, Japan
[73] Assignee: Nissan Chemical Industries, Ltd., Tokyo, Japan
[21] Appl. No.: 437,885
[22] Filed: Nov. 17, 1989

Related U.S. Application Data

[62] Division of Ser. No. 79,464, Jul. 30, 1987, Pat. No. 4,902,812.

[30] Foreign Application Priority Data

Jul. 31, 1986 [JP] Japan .................................. 61-180969
Oct. 31, 1986 [JP] Japan .................................. 61-260419
Feb. 17, 1987 [JP] Japan .................................. 62-33615

[51] Int. Cl.$^5$ ................. C07D 303/04; C07D 303/08; C07F 7/08; C07F 7/22
[52] U.S. Cl. .................................. 549/208; 549/209; 549/215; 549/513; 549/523; 549/550; 556/12; 556/87; 568/715; 568/812; 568/822; 568/838; 568/839; 568/841; 568/842; 568/843
[58] Field of Search ............... 549/208, 209, 218, 550; 568/715, 812, 822, 838, 839, 841, 842, 843; 556/12, 87

[56] References Cited

FOREIGN PATENT DOCUMENTS 0046033 2/1982 European Pat. Off. .

OTHER PUBLICATIONS

Bulletin of the Chemical Society of Japan, vol. 52(9), pp. 2646-2652 (1979), M. Obayashi et al.
Tetrahedron Letters, vol. 23, No. 52, pp. 5579-5582, 1982, Pergamon Press Ltd., A. S. Narula.
Tetrahedron Letters, vol. 24, No. 48, pp. 5421-5424, 1983, Pergamon Press Ltd., Oxford, GB, A. Narula.
Chemical Communications, Journal of the Chemical Society, No. 17, Sep. 1, 1986, pp. 1323-1325, Y. Kitano et al.
Tetrahedron Letters, vol. 28, No. 18, pp. 2033-2036, 1987, Pergamon Journals Ltd., Oxford, GB; S. Okamoto et al.
Tetrahedron Letters, vol. 28, No. 18, pp. 2041-2044, 1987, Pergamon Journals Ltd., GB; A. T. Russell et al.

Primary Examiner—Glennon H. Hollrah
Assistant Examiner—Amelia A. Owens
Attorney, Agent, or Firm—Birch, Stewart, Kolasch & Birch

[57] ABSTRACT

Provided herein is an optically active alcohol having a silyl group, stannyl group, or halogen atom at the γ-position, selected from compounds represented by the general formula [I],

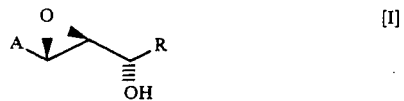

the general formula [II],

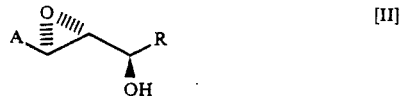

the general formula [III],

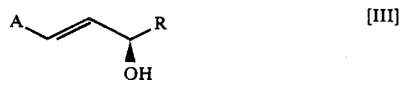

and the general formula [IV],

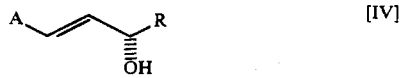

(where, R denotes a $C_1$-$C_{10}$ substituted or unsubstituted alkyl group or substituted or unsubstituted phenyl group; A denotes a silyl group represented by

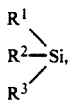

a stannyl group represented by

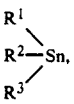

or a halogen atom, $R^1$, $R^2$, and $R^3$ are substituted or unsubstituted $C_1$-$C_{10}$ alkyl groups or substituted or unsubstituted phenyl group, which may be the same or different, provided that this does not apply in the case where A represents a stannyl group or halogen atom in the general formulas [III] and [IV].); a process for producing the same, and a process for resolving the optically active alcohol into isomers of high optical purity.

8 Claims, No Drawings

OPTICALLY ACTIVE ALCOHOLS AND PROCESS FOR PRODUCING THE SAME

This application is a divisional of copending application Ser. No. 07/079,464, filed on July 30, 1987 now U.S. Pat. No. 4,902,812.

BACKGROUND OF THE INVENTION

1. Field of the Invention

The present invention relates to an optically active alcohol having one group or atom selected from silyl group, stannyl group, and halogen atoms at the γ-position and having an epoxy group in the molecule: to a new optically active allyl alcohol having a silyl group at the γ-position: to a process for producing these optically active alcohols; and to a process for resolving these optically active alcohols having an epoxy group and these optically active allyl alcohols into their respective isomers of high optical purity.

2. Description of the Prior Art

The secondary allyl alcohol is a useful compound per se, and it has been generally regarded as a useful intermediate for synthesis. Recently, a variety of physiologically active compounds containing a skeleton of secondary allyl alcohol in the molecular structure have become well known. These compounds are mostly optically active isomers and the synthesis of optically active isomer of secondary allyl alcohol is a subject of industrial importance.

Where the desired compound to be synthesized is a mixture of complex stereoisomers containing the skeleton of optically active allyl alcohol in the molecular structure, there is a demand for optically active allyl alcohol as an advantageous intermediate that permits various reactions very easily.

For example, in the synthesis of prostaglandin compound, a drug of new type, it is known that an optically active allyl alcohol [IIc] having a halogen atom at the γ-position

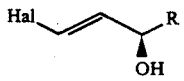

is converted into an optically active allyl alcohol [IVc] having a halogen atom at the γ-position

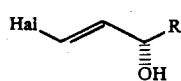

(where Hal represents a halogen atom: and R represents a saturated or unsaturated, substituted or unsubstituted alkyl group having 1–10 carbon atoms, or a substituted or unsubstituted phenyl group).

The said optically active allyl alcohol [IVc] is used as such as a raw material of the w-side chain. (See J. Org. Chem., 39 2506 (1974), by J. W. Patterson, Jr. et al.)

An optically active allyl alcohol [IVb] having a stannyl group at the γ-position

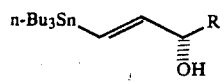

can also be used as a raw material of the ω-side chain. (See Tetrahedron Letter, 27, 2199 (1986), by E. J. Coreys, etc.

A compound of the general formula [VI] below is also reported as a raw material for the ω-side chain.

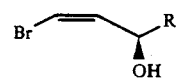

(See J. Am. Chem. Soc., 96, 6774 (1974), by J. G. Miller, W. Kurz.)

There are some known processes for the synthesis of optically active secondary allyl alcohol. For example, (1) synthesis by the asymmetric reduction of a conjugated enone [VII]. (See, for example, J. Am. Chem. Soc., 101, 5843 (1979), by Noyori et al.)

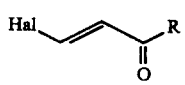

(2) synthesis by the asymmetric reduction of a conjugated inone [VIII], followed by hydroamylation and halogenation. (See J. Am. Chem. Soc., 97, 857 (1975), by C. J. Sih et al.) (3) synthesis by the asymmetric reduction of a conjugated inone, followed by hydrogenation. (See J. Am. Chem. Soc., 106, 6717 (1984), by Noyori et al.)

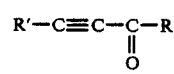

These processes, however, are industrially disadvantageous, because they need an expensive enzyme or optically active binaphthol as the asymmetric source, they provide the reaction products [IVb] and [IVc] having an optical purity lower than 97%ee, and they have to be performed with a low substrate concentration at a low reaction temperature (say, −100° C.).

On the other hand, Katsuki, Sharpless, et al. showed that a very useful process for synthesizing optically active allyl alcohols is the kinetic optical resolution process. According to this process, titanium tetraalkoxide alcohol and optically active tartaric diester are subjected to the epoxidizing reaction with a peroxide such as t-butyl hydroperoxide. (U.S. Pat. Nos. 4,471,130 and 4,594,439)

The so-called "Sharpless oxidation reaction" is superior to others in that it employs inexpensive tartaric diester as the asymmetric source. In addition, it is now more important than before because of the recent finding that the asymmetric source can be reduced to a catalytic amount. (J. Org. Chem., 51, 1922 (1986), by K. B. Sharpless et al.)

Sharpless process, however, still has some problems. First, the kinetic optical resolution of secondary allyl alcohol as disclosed by Sharpless et al. has a disadvantage that there is no satisfactory difference between the epoxidation rate of one specific optically active allyl alcohol and the rate of the other corresponding opposite optically active allyl alcohol. In other words, optically active allyl alcohol of extremely high purity cannot be obtained unless racemic allyl alcohol, a raw material for the epoxidization reaction, is epoxidized more than 60%. (See J. Am. Chem. Soc., 103, 6237 (1981), by K. B. Sharpless et al.)

This means that more than 60% of racemic allyl alcohol, a raw material, is wasted when optically active secondary allyl alcohol of use is to be obtained. This step lowers the yield to less than 40% in the commercial production. After subsequent many complex steps, the final yield of the desired product would be very low.

Secondly, the allyl alcohol disclosed by Sharpless et al. is of less practical use because the cis-isomer is extremely poor in optical resolution.

Thirdly, in the case of allyl alcohol as disclosed by Sharpless et al., there is no example of reaction substrate such as a compound having an electron-withdrawing halogen atom (e.g., a compound [IX] having a bromine atom) and a compound having an easily oxidizable atom (e.g., a compound having a sulfur atom [X] and a compound having a tin atom [Vb]). There is a possibility that the epoxidizing reaction itself does not proceed. Therefore, it could not be an effective kinetic optical resolution process.

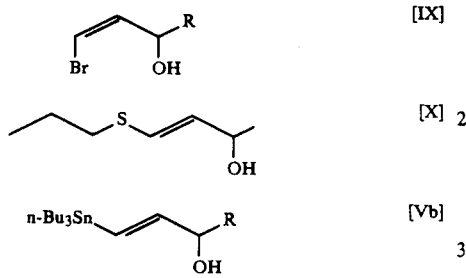

The conceivable reason why the epoxidizing reaction itself does not proceed is that halo-olefins are generally slow in oxidization because the double bond has a low electron density, and that there is a possibility that the oxidation of a tin atom, halogen atom, or sulfur atom is faster than that of olefins.

The other possible reason is that the epoxy alcohol [I] or [II] considered as a reaction product is extremely unstable.

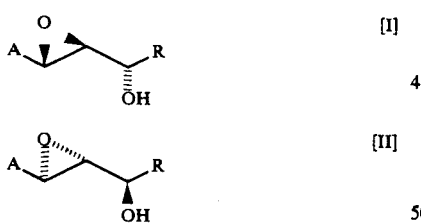

The epoxy alcohol is a useful compound per se, and it is also useful as an intermediate for synthesis, because physiologically active compounds containing an optically active epoxy group in the molecular structure have recently been increasing and a compound such as optically active secondary allyl alcohol and optically active 1,2-diol and 1,3-diol which is obtained by the stereospecific reaction at the optically active epoxy group.

However, the optically active epoxy alcohols [I] and [II] having an easily convertible atom such as silicon, tin, and halogen at the γ-position have not been known, and this has been a great hindrance for industrial use.

SUMMARY OF THE INVENTION

The present invention is intended to eliminate the above-mentioned three disadvantages of Sharpless process. Accordingly, it is an object of the present invention to provide new useful optically active alcohols, a process for producing the same, and a process for resolving the same.

The present invention is based on the finding that if the trans-allyl alcohol having a silyl group, stannyl group, or halogen atom at the γ-position [V]

is oxidized in the presence of titanium tetraalkoxide and an optically active tartaric diester, the following reactions proceed at a high rate of optical resolution which has never been achieved before and optically active epoxy alcohol [I] and optically active allyl alcohol [III] of anti-form, or optically active epoxy alcohol [II] and optionally active allyl alcohol [IV] of anti-form are obtained.

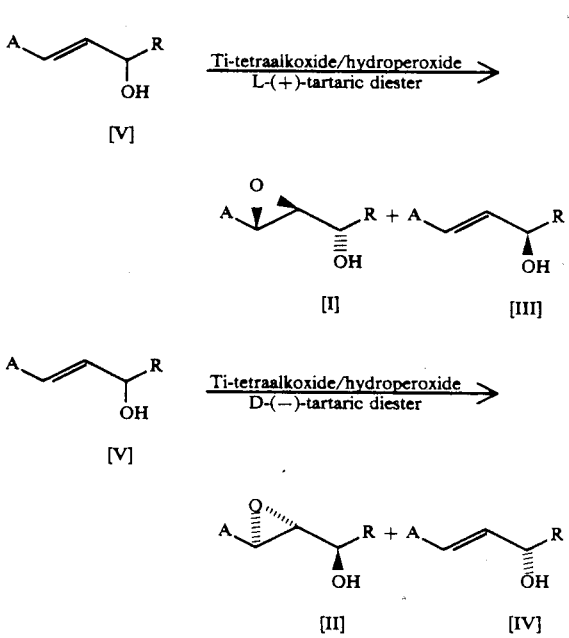

It is an object of the present invention to provide an optically active alcohol having a silyl group, stannyl group, or halogen atom at the γ-position, selected from compounds represented by the general formula [I],

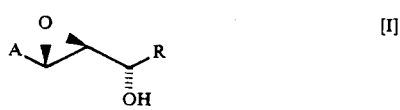

the general formula [II],

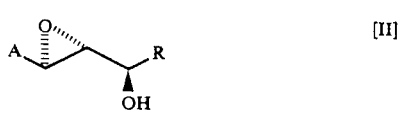

the general formula [III], and the general formula [IV],

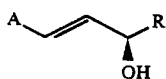

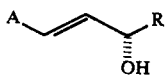

(where, R denotes a $C_1$–$C_{10}$ substituted or unsubstituted alkyl group or substituted or unsubstituted phenyl group; A denotes a silyl group represented by

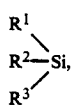

a stannyl group represented by

or a halogen atom. $R^1$, $R^2$, and $R^3$ are substituted or unsubstituted $C_1$–$C_{10}$ alkyl groups or substituted or unsubstituted phenyl group, which may be the same or different, provided that this does not apply in the case where A represents a stannyl group or halogen atom in the general formulas [III] and [IV].)

It is another object of the present invention to provide a process for producing an optically active alcohol having a silyl group, stannyl group, or halogen atom at the γ-position, selected from compounds represented by the general formulas [I], [II], [III], and [IV] above, said process comprising oxidizing trans-allyl alcohol having a silyl group, stannyl group, or halogen atom at the γ-position, selected from the compounds represented by the general formula [V]

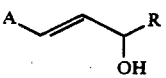

(where, R denotes a $C_1$–$C_{10}$ substituted or unsubstituted alkyl group or substituted or unsubstituted phenyl group; A denotes a silyl group represented by

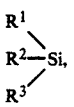

a stannyl group represented by

or a halogen atom. $R^1$, $R^2$, and $R^3$ are substituted or unsubstituted $C_1$–$C_{10}$ alkyl groups or substituted or unsubstituted phenyl group, which may be the same or different.) with hydroperoxide in the presence of titanium tetraalkoxide and optically active tartaric diester.

It is further another object of the present invention to provide a process for resolving thus obtained optically active alcohols.

The alcohols represented by the general formulas [I], [II], [III], and [IV] are effective for the synthesis of complex physiologically active substances containing in their skeleton highly stereocontrolled secondary alcohol, epoxy alcohol, or 1,2- or 1,3-diol which have not been easily obtained by the conventional Sharpless process and other processes.

One of the features of the present invention is the high efficiency of optical resolution. When the (racemic) secondary allyl alcohol having a silyl group, stannyl group, or halogen atom at the γ-position [V] is oxidized with hydroperoxide in the presence of titanium tetraalkoxide and optically active tartaric diester, one of the optical isomers undergoes the epoxidizing reaction rapidly and the other undergoes the epoxidizing reaction very slowly in response to the optical structure of the tartaric diester used. After the completion of epoxidizing reaction for a practical period of time, say 7 hours, the resulting epoxy compound has an optical purity higher than 99% and the allyl alcohol remaining unreacted has also an optical purity higher than 99%. This high optical purity of the reaction product does not change any more even though the reaction time is extended to 10 hours.

This means that one of the optical isomers of the racemic compound [V] susceptible to epoxidizing undergoes the epoxidizing reaction almost completely in response to the optical structure of the tartaric diester used and subsequently the other optical isomer of the racemic compound [V] susceptible to epoxidizing begins to undergo the epoxidizing reaction very slowly. The ratio of the two reaction rates is almost infinitely large. Table 1 below shows the relationship between the reaction time and the optical purity in the following reaction.

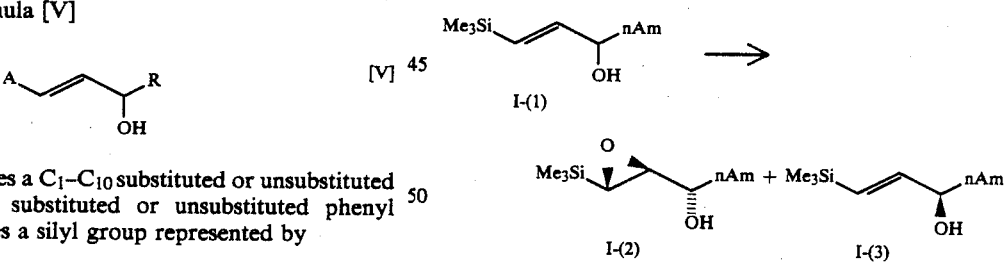

(where Me denotes a methyl group and nAm denotes an n-amyl group.)

TABLE 1

| Reaction time (hr) | Optical Purity | |
|---|---|---|
| | Compound I-(2) | Compound I-(3) |
| 7 | >99 | >99 |
| 10 | 99 | >99 |
| 18 | 98 | >99 |

Table 1 may be interpreted as follows from a practical point of view. The reaction in question can be controlled very easily because the optical isomers in the racemic compound undergo epoxidizing reaction at quite different rates whose ratio is almost infinitely large. In the case of prior art when the reaction is suspended, the conversion of epoxidization has reached 60% (based on the racemic reaction substrate). Monitoring to judge when to stop the reaction at a high yield of chiral allyl alcohol requires a lot of labor and causes a loss of reaction product. According to the process of this invention, the reaction can be controlled simply by regulating the reaction time with a great latitude, because the ratio of reaction rate is extremely great, almost infinite. For example, in the case of optically active allyl alcohol obtained in Examples 28 and 29, the reaction ratio is 49% (optical purity >98%ee) and 51% (optical purity >99%ee) after a reaction time of 14 hours and 38 hours, respectively. Thus suggests that it is possible to reduce the amount of oxidizing agent to a minimum or conversely to increase to a large excess. The control of reaction temperature becomes easier. For example, the reaction temperature of +20° C. is now possible. (According to the conventional process, the reaction temperature was −25° C. to −20° C.) (See Table 7.) The mild reaction conditions are of great industrial advantage.

Secondly, the process of this invention permits the production of epoxy alcohol of high optical purity. These new optically active epoxy alcohols [1] and [11] obtained according to the following equations

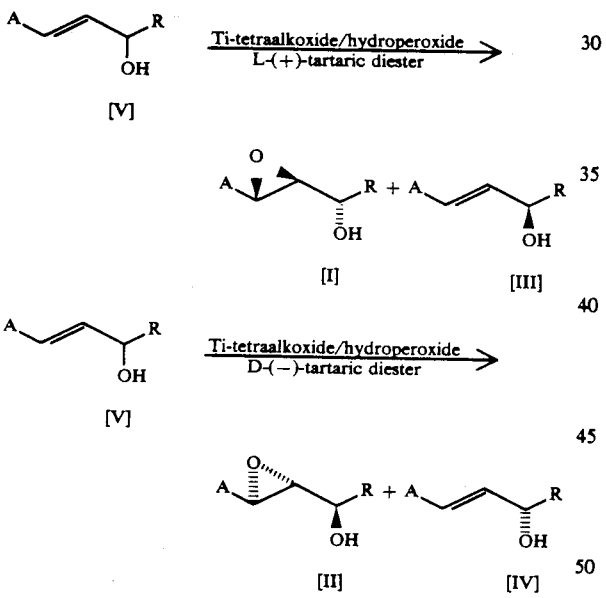

have an optical purity higher than 98% on account of the silyl group, stannyl group, and halogen atom at the γ-position. [I] and [II] may be used as such or converted into optically active allyl alcohol or 1,2- or 1,3-diol. They may also be converted into optically active allyl alcohol as mentioned later. In other words, in the case of conventional Sharpless process, about one half (usually more than 60%) of racemic allyl alcohol as a raw material becomes an epoxy compound, but the resulting epoxy alcohol has a low optical purity, say 90%ee at the highest. It is too crude to be a raw material for chiral synthesis. In order to obtain epoxy alcohol of high optical purity, it was necessary to further epoxidize the optically active allyl alcohol (to make a mixture of syn-form and anti-form). By contrast, the epoxy alcohol obtained in the present invention has an optical purity higher than 98%ee, and it is composed mainly of anti-form alone.

Moreover, as mentioned later, the resulting epoxy alcohol can also be readily converted into optically active allyl alcohol. In other words, the raw material compound [V] having a silyl group, stannyl group, or halogen atom at the γ-position is entirely used effectively, i.e., a half is used for optically active allyl alcohol and remaining half is used for optically active epoxy alcohol. This is the second feature of the invention.

The third feature of the invention is that the optically active alcohols [I], [II], [III], and [IV] obtained in the invention are new compounds having a silyl group, stannyl group, or halogen atom at the γ-position (except [III] and [IV] in which A is a stannyl group or halogen atom). These hetero atoms permit the compounds to be derived into various useful compounds such as the w-side chain for prostaglandins and leukotrien B4 (LTB4).

The additional feature of the present invention is that the epoxidation of the compound [V] proceed more rapidly than in the case of conventional Sharpless process. And moreover, the reaction time of the invention process can be more shortened to such 10–20 hours by the increase of amount of peroxide and by the raise-up of the reaction temperature which can be able because of the first feature, where the reaction time are 5–15 days in the case of conventional Sharpless reaction. This is very important as an industrial process.

What is important to obtain the new useful optically active alcohols [I], [II], [III], and [IV] of high optical purity is to use a compound represented by the formula [V] below.

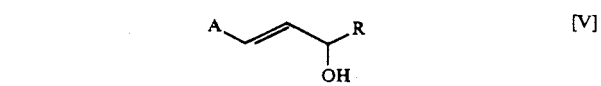

(where A is a silyl group, stannyl group, or halogen atom.) and R are defined as above.) In other words, the feature of the present invention resides in using a trans-secondary allyl alcohol having a silyl group, stannyl group, or halogen atom at the γ-position.

As will be understood from the foregoing. [I] and [II] can be also synthesized from [III] or [IV] as shown below.

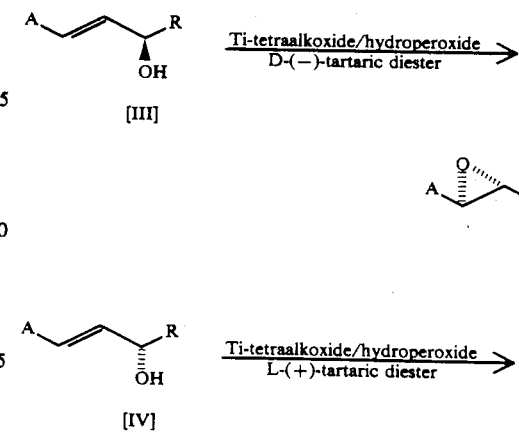

DETAILED DESCRIPTION OF THE INVENTION

According to the process of the present invention, there are obtained new optically active alcohols represented by the following formulas [I], [II], [II], and [IV].

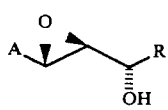   [I]

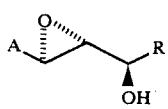   [II]

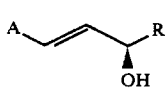   [III]

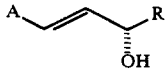   [IV]

R in the above formulas denotes a $C_1$–$C_{10}$ substituted or unsubstituted alkyl group or substituted or unsubstituted phenyl group. It includes, for example, methyl, ethyl, n-propyl, i-propyl, n-butyl, i-butyl, t-butyl, amyl, isoamyl hexyl, heptyl, octyl, nonyl, decyl, 2-methylhexyl, 2-methyl-2-hexyl, 2-hexyl, cyclopentyl, cyclohexyl, cyclohexamethyl, hex-4-yn-2-yl, hept-4-yn-2-yl, hept-4-yn-2-yl, 2,6-dimethyl-hept-5-en-1-yl, pent-1-en-1-yl, pent-2-en-1-yl, hex-1-en-2-yl, 3-ethoxy-2-methylpropan-2-yl, methoxyethyl, 5-methoxyhexyl, 6-methoxy-2-hexyl, halogenated methyl, halogenated n-butyl, halogenated n-pentyl, halogenated nonyl, phenyl, halogenated phenyl, n-pentyloxymethyl, 1-ethoxy-2-methylpropan-2-yl, phenoxymethyl, benzyloxymethyl, p-chlorophenoxymethyl, 2-phenylethyl, benzyloxyethyl, p-fluorophenoxymethyl, phenylacetylenyl, m-chloro-phenoxymethyl, m-trifluoromethyl-phenoxymethyl, 1-butyl-cyclopropyl, 3-ethyl-cyclopentyl, benzothiophen-5-yl, 2-octenyl, 3-methoxycarbonylpropyl, and vinyl.

A at the γ-position denotes a silyl group represented by

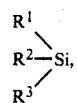

a stannyl group represented by

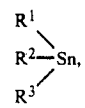

or a halogen atom. If A is a silyl group, the optically active allyl alcohols represented by the general formulas [III] and [IV] are new substances, but if A is a stannyl group or halogen atom, the optically active allyl alcohols represented by the general formulas [III] and [IV] are partly known compounds. $R^1$, $R^2$, and $R^3$ are substituted or unsubstituted $C_1$–$C_{10}$ alkyl groups or substituted or unsubstituted phenyl group, which may be the same or different. They include, for example, methyl, ethyl, n-propyl, i-propyl, n-butyl, i-butyl, t-butyl, amyl, hexyl, heptyl, octyl, nonyl, decyl, phenyl, p-tolyl, m-chlorophenyl, and p-methoxyphenyl. The halogen atom includes, for example, iodine atom, bromine atom, and chlorine atom.

The titanium tetraalkoxide used in the invention includes, for example, titanium tetramethoxide, titanium tetraethoxide, titanium tetrapropoxide, titanium tetraisopropoxide, titanium tetrabutoxide, and titanium tetra-t-butoxide. They may be used individually or in combination with one another. They should preferably be used in an amount of 0.05–1.0 mol for 1 mol of the allyl alcohol represented by the general formula [V].

According to the process of the invention, the optically active alcohols represented by the general formulas [I], [II], [III], and [IV] are obtained by using an optically active tartaric diester which controls the optical activity of the reaction products. If an L-(±)-tartaric diester is used, the following reaction takes place.

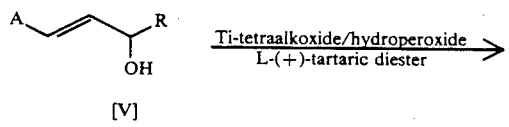

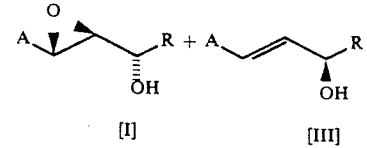

If a D-(−)-tartaric diester is used, the following reaction takes place.

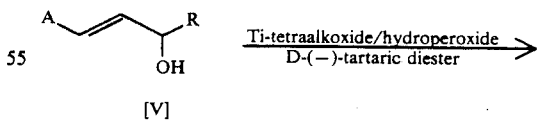

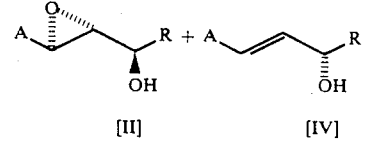

The reaction gives very little syn-epoxy alcohol which is a diastereoisomer of [I] and [II]. The optically active tartaric diester used in this reaction includes, for example, dimethyl L-(+)-tartrate, diethyl L-(+)-tartrate, diisopropyl L-(+)-tartrate, di-t-butyl L-(+)-tartrate, distearyl L-(+)-tartrate, and diphenyl L-(+)-tartrate, and D-(−)-isomers thereof.

The tartaric diester should be used in an amount of 0.9–2.0 mol, preferably 1.0–1.2 mol, for 1 mol of the above-mentioned titanium alkoxide.

The oxidizing agent used in this reaction is usually hydroperoxide such as t-butyl hydroperoxide, α,α-dimethylheptyl hydroperoxide, bis-isobutyl-2,5-dihydroperoxide, 1-methylcyclohexyl hydroperoxide, cumene hydroperoxide, and cyclohexyl hydroperoxide. It should be used in an amount of 0.5–3 mol, preferably 0.5–1.5 mol, for 1 mol of the allyl alcohol [V].

The process of the invention should preferably be carried out in a solvent, preferably an inert solvent, particularly a halogenated hydrocarbon solvent. It includes, for example, dichloromethane and dichloroethane.

The reaction temperature is in the range of −80° C. to 80° C. preferably −30° C. to 30° C. The reaction time is usually 10 minutes to 100 hours, depending on the reaction substrate and reaction temperature used.

Since the reaction system is apt to be easily damaged by moisture, it is necessary to dehydrate the reaction solvent, reaction substrate, and reactants as far as possible. In the case where a catalytic amount of tartaric diester is used, the reaction may be carried out in the presence of pulverized molecular sieve, calcium hydride, and silica gel.

The trans-allyl alcohol [V] used in the invention may

[V]

be racemic or a mixture of optically active isomers. In the case where optically active epoxy alcohol [I] or [II] is synthesized, it is possible to use the corresponding optically active allyl alcohol [IV] or [III], respectively.

In the meantime, [V] can be synthesized in the usual way by (1) ketone reduction of enone, (2) reaction of vinyl metal reagent and aldehyde, or (3) trans-hydrogenation of acetylene alcohol.

In what follows, a description will be made of the usefulness of the compounds [I], [II], [III], and [IV] of the present invention. Their usefulness derives from their being a chiral compound and their having a vinyl silyl group (or vinyl stannyl group or vinyl halogeno group) or an epoxy silyl group, epoxy stannyl group, or epoxy halogeno group. According to the process of the invention, the optically active allyl alcohol of cis-form, which cannot be efficiently obtained by the conventional Sharpless process or other process, can be easily obtained from the silyl group-containing compound [I], [II], [III], and [IV] of the invention by utilizing the known reaction of vinylsilyl group or epoxysilyl group. (E. W. Colvin, "Silicon in Organic Synthesis", Butterworths, London (1981): W. P. Webber, "Silicon Reagents for Organic Synthesis", Springer-Verlag, New York (1983)) For example, a halogen-bearing compound [VI] (which is used as the ω-side chain of prostaglandin) can be easily obtained.

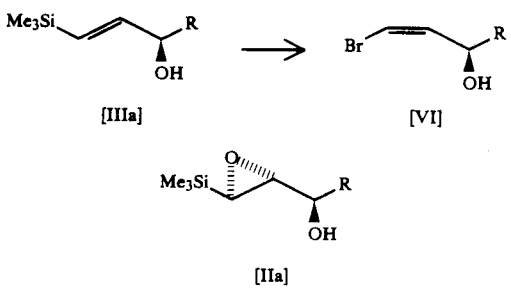

The usefulness of the compounds [Ia], [IIa], [IIIa], and [IVa] having a vinylsilyl group or epoxysilyl group are illustrated by the following reactions.

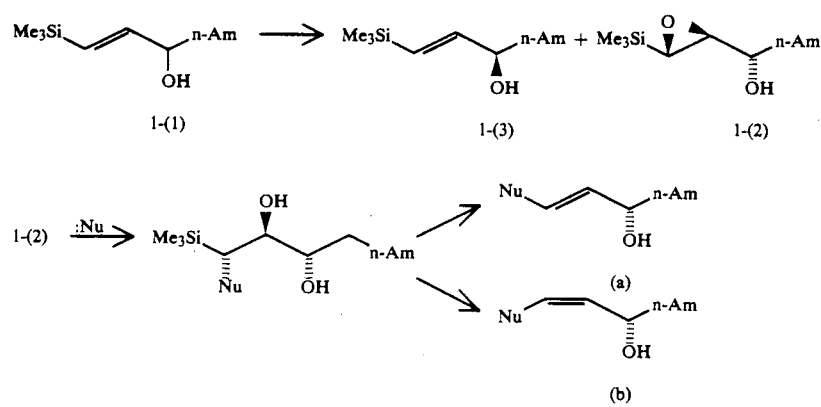

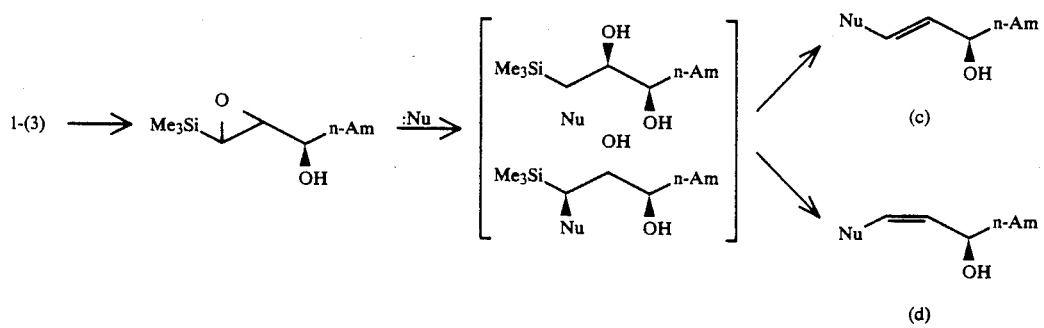

In the above formulas, Nu represents a nucleophilic reagent such as alkyl anion, halogen anion, and mercapto anion. All of the compounds (a), (b), (c), and (d) are four optically active allyl alcohols which are theoretically possible. In other words, the new compounds [I], [II], [III], and [IV] of the present invention permit the synthesis of all the optically active isomers of various kinds of secondary allyl alcohols as shown in the following.

1,2-Diols represented by the general formula [XI] can be also obtained by reacting an epoxy alcohol of anti-form (with the hydroxyl group protected) represented by the general formula [Ia] with a Grignard's reagent.

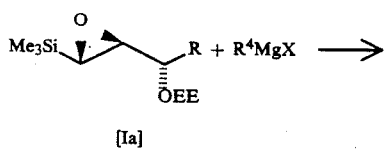

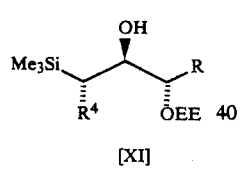

(where, R is as defined above; and $R^4$ denotes a $C_1$–$C_{10}$ substituted or unsubstituted alkyl group or allyl group, or a derivative thereof.)

The compound of the general formula [XI] provides compounds represented by the general formulas [A] and [B] upon basic Peterson elimination reaction and acidic Peterson elimination reaction, respectively.

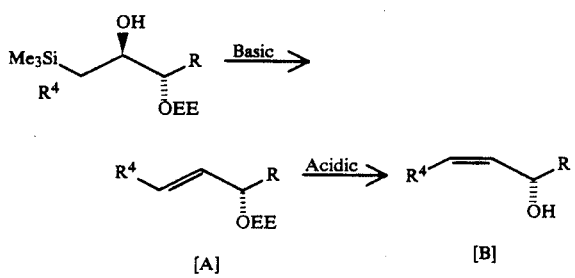

A similar reaction is also noticed in the reaction of anti-epoxy alcohol having a stannyl group at the γ-position (represented by the general formula [Ib]) with an organotin lithium reagent. It is possible to obtain optically active allyl alcohol [IVb] according to this reaction.

The silyl group-bearing [Ia] can be converted into an unsubstituted epoxy alcohol [XII] by protecting the hydroxy group, treating with tetrabutyl ammonium fluoride, with the hydroxyl group protected, and then removing the protection, or the iodine atom (halogen atom)-bearing [Ic] can be converted into an unsubstituted epoxy alcohol [XII] by treating with tri-n-butyltin hydride.

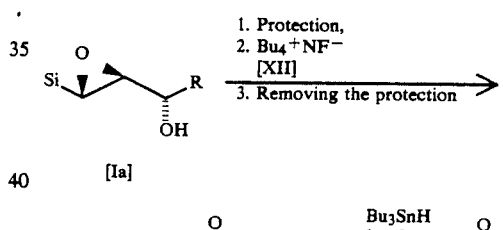

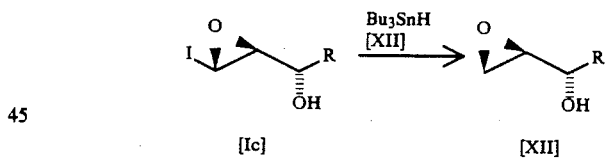

The unsubstituted epoxy alcohol [XII] is a useful compound for the synthesis of brevicomin (an insect pheromone) (S. Takano et al., J. C. S., Chem. Commun., 1985, 1759) and monosaccharide (D. Seebach et al., Helv. Chim. Acta, 64., 687, (1981)).

In addition, it is also known that an optically active 1,3-diol can be obtained by the Red-Al reduction of an optically active epoxy alcohol similar to [I] or [II]. (I. O. Sutherland et al., Tetrahedron Let., 27, 3535 (1986)) This reaction can also be utilized.

Furthermore, when the allyl alcohol of trans-form represented by the general formula [III] which has a hydroxyl group of restricted configuration and also has a silyl group, stannyl group, or halogen atom at the γ-position undergoes the ordinary epoxidizing reaction, both epoxy alcohol of syn-form and epoxy alcohol of anti-form represented by the general formula [C] are obtained. If the one of anti-form alone is desired, the epoxidizing reaction of the invention should be performed which uses a corresponding optically active tartaric diester.

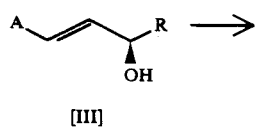

[III]

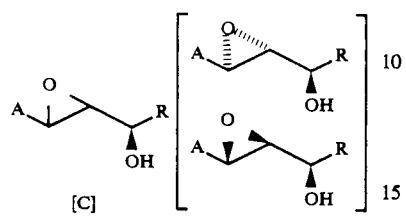

[C]

If A is a silyl group, the thus obtained compound represented by the general formula [C] (regardless of whether syn-form or anti-form) provides compounds of the general formulas [D] and [E] upon reaction with R⁴MgX, with the hydroxyl group protected or ethoxymethylated, followed by basic Peterson elimination reaction or acid Peterson elimination reaction.

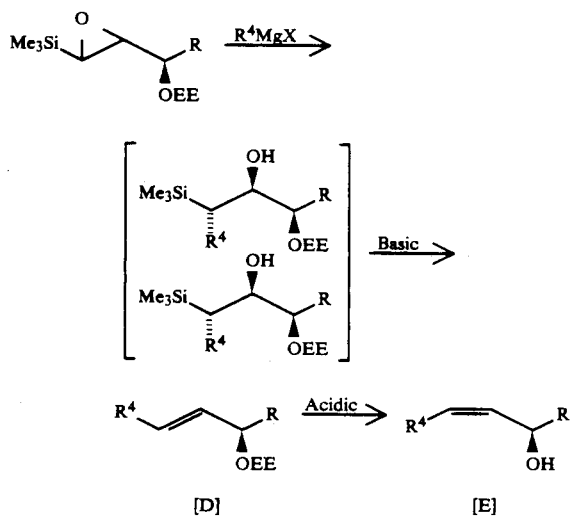

In other words, if the compound of the invention is used as a starting material, it is possible to synthesize as desired the compounds represented by the general formulas [D] and [E] can be synthesized (all the stereo isomers of optically active allyl alcohol).

The above-mentioned reaction can be applied to epoxy alcohol of anti-form as well as allyl alcohol of trans-form having a silyl group, stannyl group, or halogen atom at the γ-position and also having a hydroxyl group with restricted configuration as in [II] for [I] and [IV] for [III]. Thus it is possible to obtain highly stereocontrolled compounds.

The highly stereocontrolled alcohols represented by the general formulas [I], [II], [III], and [IV] in the present invention are new compounds. They are useful as an intermediate for the synthesis of physiologically active substances. They are physiologically active per se.

According to the process for producing the alcohols of the present invention represented by the general formulas [I], [II], [III], and [IV] makes it possible to produce allyl alcohol and epoxy alcohol having a silyl group, stannyl group, or halogen atom at the γ-position,
at a high optical purity and high yield in a stable manner with a high selectivity.

To further illustrate the invention, and not by way of limitation, the following examples are given.

It should be noted in the following examples that Me shows methyl group, Ph shows phenyl group, Bu shows butyl group, Am shows amyl group, and Ac shows acetyl group.

EXAMPLE 1

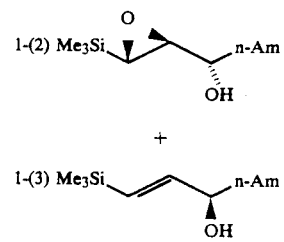

In 40 ml of dichloromethane were dissolved 4.48 mmol of titanium tetraisopropoxide and 5.38 mmol of diisopropyl L-(+)-tartrate. To the solution (cooled to −20° C.) was added 3 ml of dichloromethane solution containing 0.895 g (4.48 mmol) of the compound 1-(1) under an argon atmosphere, followed by stirring for 10 minutes.

Then, 2.6 ml of dichloromethane solution containing 6.72 mmol of t-butyl hydroperoxide (TBHP) was added, followed by stirring for 6–7 hours at −20° C. With the addition of 1 ml of dimethyl sulfide, stirring was continued for 30 minutes. To the resulting solution were added 3 ml of 10% aqueous solution of tartaric acid, 40 ml of diethyl ether, 3 g of sodium fluoride, and 2 g of Celite, followed by stirring at room temperature. The reaction mixture was filtered and the residue was washed with 10 ml of diethyl ether. The washings were combined with the filtrate. The filtrate was distilled under reduced pressure to remove the solvent. Thus there was obtained a crude product. The crude product was purified by silica gel chromatography to give 387 mg (40% yield) of the compound 1-(2) and 358 mg (40% yield) of the compound 1-(3). The compounds 1-(2) and 1-(3) had the optical purity as shown in Table 1. The following are the values of analysis of the compounds 1-(2) and 1-(3).

Compound 1-(2)

¹H NMR (CCl₄ (solvent), PhH (internal standard), D₂O (added)): δ 0.03 (s, 9H, 3(CH₃)Si), 0.93 (t, J=4.8 Hz, 3H, CH₃), 1.07–1.72 (m, 8H, 4CH₂), 2.26 (d, J=4.0 Hz, 1H, SiCHO), 2.71 (t, J=4.0 Hz, 1H,

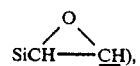

3.30–3.70 (m, 1H, CHO).

IR: 3410, 2930, 1247 cm⁻¹.

[α]$_D^{25}$: −7.4° (C 1.05, CHCl₃).

Compound 1-(3)

$^1$H NMR (CCl$_4$, PhH, D$_2$O): δ 0.07 (s, 9H, 3(CH$_3$)Si), 0.94 (t, J=6.0 Hz, 3H, CH$_3$), 1.10-1.75 (m, 8H, 4CH$_2$), 3.93 (q, J=4.8 Hz, 1H, CHO), 5.67 (d, J=18.0 Hz, 1H, SiCH), 6.00 (dd, J=4.8, 18.0 Hz, 1H, CH=CHSi).

$^{13}$C NMR (CDCl$_3$): −1.3, 13.9, 22.5, 25.0, 31.8, 36.9, 74.6, 128.8, 148.9

IR: 3330, 2930, 1645, 1285 cm$^{-1}$.

b.p.: 90° C./3 mmHg.

[α]$_D^{25}$: −9.5° (C 1.45, CHCl$_3$)

EXAMPLE 2

The same procedure as in Example 1 was repeated except that the reaction time was changed to 10 hours. Thus there were obtained the compounds 1-(2) and 1-(3). The results are shown in Table 1.

EXAMPLE 3

The same procedure as in Example 1 was repeated except that the reaction time was changed to 18 hours. Thus there were obtained the compounds 1-(2) and 1-(3). The results are shown in Table 1.

TABLE 1

| Example | Reaction time (hr) | Optical Purity (% ee) Compound 1-(2) | Compound 1-(3) |
| --- | --- | --- | --- |
| 1 | 7 | >99 | >99 |
| 2 | 10 | 99 | >99 |
| 3 | 18 | 98 | >99 |

It is noted from Table 1 that the prolonged asymmetric epoxidizing reaction affects very little the optical purity of the compounds 1-(2) and 1-(3).

EXAMPLE 4

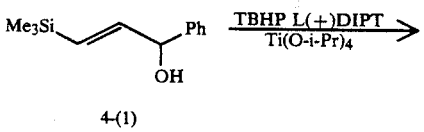

4-(1)

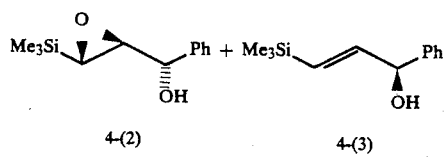

4-(2)  4-(3)

To 170 ml of dichloromethane (CH$_2$Cl$_2$) solution (cooled to −23° C.) containing 5.8 ml (19.4 mmol) of titanium tetraisopropoxide (Ti(OiPr).$_4$) was slowly added dropwise 4.7 ml (23.3 mmol) of diisopropyl L-(±)-tartrate, followed by stirring for 10 minutes. To the resulting solution was added dropwise 10 ml of dichloromethane solution containing 4 g (19.4 mmol) of the compound 4-(1), followed by stirring for 10 minutes. Then 11.9 ml (29.1 mmol) of t-butyl hydroperoxide (TBHP) (at a concentration of 2.44 in CH$_2$Cl$_2$) was added, followed by stirring for 4 hours. 2.8 ml (38.8 mmol) of Me$_2$S was added at −23° C., followed by stirring for 20 minutes at the same temperature. The solution was warmed to room temperature, and 5 ml of 10 wt % aqueous solution of tartaric acid and 20 ml of ethyl ether were added, and finally 8 g was NaF was added, followed by stirring for 30 minutes. The precipitates were removed by filtration through Celite and the solvent was distilled away under reduced pressure. The crude reaction product was purified by silica gel chromatography to give 1.87 g of the compound 4-(2) and 1.72 g of the compound 4-(3). The data of $^1$H NMR indicated that the reaction proceeded 50% almost quantitatively.

The compound 4-(3) was epoxidized for 6 hours under the above-mentioned conditions and further for 1 hour at 0° C.: but no reaction product appeared on TLC.

The values of analysis of the compounds 4-(2) and 4-(3) are shown below.

Compound 4-(2)

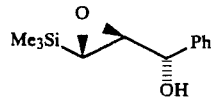

$^1$H NMR (CCl$_4$, CH$_2$Cl$_2$, D$_2$O): δ −0.05 (s, 9H, (CH$_3$)$_3$Si), 2.44 (d, J=4.0 Hz, 1H,

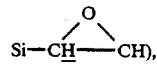

2.95 (t, J=4.0 Hz, 1H,

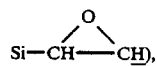

4.63-4.83 (m, 1H, CHOH), 7.16-7.46 (m, 5H, Ar).

IR (neat): 3400, 2975, 1940, 1605, 1250, 838, 695 (cm$^{-1}$).

$^{13}$C NMR (CDCl$_3$): 140.2, 128.3, 127.9, 126.4, 72.1, 58.9, 47.8, −3.8.

[α]$_D^{25}$: +25.7° (C 1.58, CHCl$_3$).

Compound 4-(3)

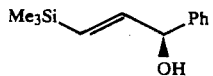

$^1$H NMR (CCl$_4$, CH$_2$Cl$_2$, D$_2$O): δ 0.17 (s, 9H, (CH$_3$)$_3$Si), 5.05 (d, J=4.6 Hz, 1H, CHO) 5.93 (d, J=19.8 Hz, 1H, SiH=CH) 6.23 (dd, J=4.6, 19.8 Hz, 1H, SiCH=CH), 7.10-7.54 (m, 5H, Ar).

IR (neat): 3320, 2960, 1605, 1250, 839, 695 (cm$^{-1}$).

$^{13}$C NMR (CDCl$_3$): 147.3, 142.7, 129.7, 128.4, 127.4, 126.4, 76.6, −1.4.

[α]$_D^{25}$: −10.8° (C 1.06, CHCl$_3$).

bp. 108°-111° C./0.32 mmHg Elemental analysis for C$_{12}$H$_{18}$OS: Calcd. C, 69.85: H, 8.79 Found. C, 69.71: H, 8.90.

EXAMPLES 5 To 9

The same procedure as Example 1 was repeated. The results are shown in Table 2 below.

TABLE 2

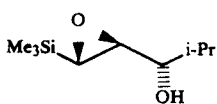

| Example No. | A | R | Reaction time (hr) | Optical purity and (yield) (2) | (3) |
|---|---|---|---|---|---|
| 5 | Me₃Si | iPr | 6 | >99% ee (49%) | 99% ee (49%) |
| 6 | Me₃Si | CH₂OPh | 13 | >99% ee (47%) | >99% ee (46%) |
| 7 | Me₃Si | CH₂OCH₂Ph | 9.5 | >99% ee (43%) | >99% ee (48%) |
| 8 | Me₃Si | 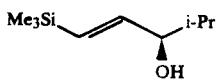 n-Am | 4 | >99% ee (44%) | >99% ee (44%) |
| 9 | Me₃Si | CH₂CH₂OCH₂Ph | 9 | >99% ee (45%) | >99% ee (43%) |

The following are values of analysis of each compound. Compound 5-(2)

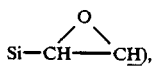

Colorless oil
$^1$H NMR (CDCl₃).

δ 0.04 (s, 9H, (CH₃)₃Si), 0.94 and 0.95 (2d, J=6.6 Hz and 6.8 Hz, 6H, (CH₃)₂C), 1.48–2.05 (m, 1H, CH(CH₃)₂), 1.98 (brs, 1H, OH), 2.35 (d, J=3.7 Hz, 1H, $$\text{Si—CH} \underset{\text{O}}{\triangle} \text{CH)},$$

2.87 (dd, J=3.1, 3 73 Hz, 1H, $$\text{Si—CH} \underset{\text{O}}{\triangle} \text{CH)},$$

3.48–3.68 (m, 1H, CHOH).
IR (neat) 3425, 2950, 1250, 840 (cm⁻¹).
$[\alpha]_D^{25}$ −1.07° (C 1.49, CHCl₃) (99 %ee).

Compound 5-(3)

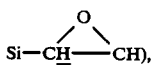

Colorless oil
$^1$H NMR (CCl₄, CH₂Cl₂) δ 0.07 (s, 9H, (CH₃)₃Si), 0.98 (d, J=7.0 Hz, 6H, (CH₃)₂CH), 1.33–1.96 (m, 1H, CH(CH₃)₂), 2.58 (brs, 1H, OH), 3.74 (t, 5.0 Hz. 1H. CHO), 5.80 (d, J=19.0 Hz, 1H, SiCH=CH), 5.95 (dd, J=5.0, 19.0 Hz, 1H, SiCH=CH).
IR (neat) 3340, 2870, 1615, 1240, 985, 840 (cm⁻¹).
$[\alpha]_D^{25}$ −21.8° (C 1.14, CHCl₃).
bp. 42°–48° C./0.1 mmHg.

Compound 6-(2)

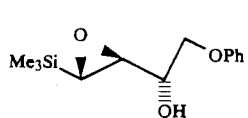

Colorless crystal
$^1$H NMR (CCl₄, CH₂Cl₂) δ 0.19 (s, 9H, (CH₃)₃Si), 2.36 (d J=3.7 Hz, 1H, SiCH(O)), 2.80 (brs, 1H, OH), 2.95–3.12 (m, 1H, SiCHCH(O)), 3.73–4.37 (m, 3H CHO and CH₂OPh), 6.74–7.45 (m, 5H, Ph).
$^{13}$C NMR (CDCl₃) δ 158.6. 129.5, 121.3, 114.7, 69.8, 69.5, 55.7, 48.8, −3.7.
mp. 61.5°–62.5° C. (recrystallized from pentane-ether).
IR (nujol) 3400, 1598, 1585, (cm⁻¹).
$[\alpha]_D^{25}$ −17.0° (C 0.978, CHCl₃).

Compound 6-(3)

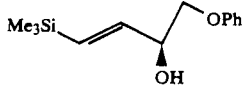

Colorless crystal
$^1$H NMR (CCl₄, CH₂Cl₂) δ 0.25 (s, 9H, (CH₃)₃Si), 2.83 (brs, 1H, OH), 3.93 and 4.04 (2dd, J=7.8, 10.2 Hz and 4.0, 10.2 Hz, 2H, CH₂OPh), 4.48–4.82 (m, 1H, (HOH) 6.21 (s, 2h, HC=CH), 6.85–7.48 (m, 5H, Ph).
$^{13}$C NMR (CDCl₃) δ 158.5, 143.4, 131.9, 129.3, 121.0, 114.6, 72.3, 71.7, −1.4.
IR (nujol) 3430, 1598, 1585, (cm⁻¹).
mp. 49.0°–50.0° C. (recrystallized from pentane-ether)
$[\alpha]_D^{25}$ +8.0° (C 1.55, CHCl₃)

REFERENCE

Compound 6-(1)

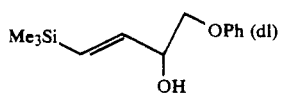

Colorless oil bp. 150°–160° C. (0.15 mmHg).
Data of NMR are the same to the compound 6-(3).

Compound 7-(2)

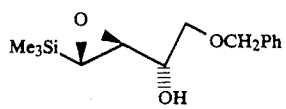

Colorless oil
¹H NMR (CCl₄, CH₂Cl₂, D₂O): δ 0.05 (s, 9H, 3CH₃), 2.17 (d, J=3.6 Hz, 1H,

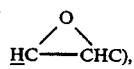

2.78 (dd, J=3.6 Hz,
3.43–3.73 (m,3h, ch(O)ch₂O), 4.46 (s,2h) ch₂ph), 4.2 Hz, 1H,

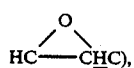

7.13–7.34 (m, aromatic).
IR (neat) 3400, 1240, 1100, 730, 690 (cm⁻¹).
[α]$_D^{25}$ −2.2° (CHCl₃, C 1.2).
Rf 0.28 (hexane/ether=1/1).

Compound 7-(3)

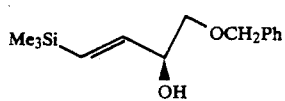

Colorless oil
¹H NMR (CCl₄, CH₂Cl₂, D₂O): δ 0.15 (s, 9H, 3CH₃), 3.32 (dd, J=7.8 Hz, 10.3 Hz, 1H, HCHO), 3.42 (dd, J=4.1 Hz, 10.3 Hz, 1H, HCHO), 4.15–4.36 (m, 1H, CHO), 4.50 (s, 2H, CH₂Ph), 5.95–6.10 (m, 2H, HC=CH), 7.23–7.40 (m, 5H, Aromatic).
IR (neat) 3400, 1245, 630, 730, 690 (cm⁻¹).
[α]$_D^{25}$ −1.9° (CHCl₃, C 1.06).
Rf 0.38 (hexane/ether=1/1).

Compound 8-(2)

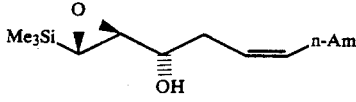

Colorless oil
¹H NMR (CCl₄, PhH): δ 0.09 (s, 9H, Si(CH₃)₃), 0.90 (t, 3H, CH₂CH₃), 2.03 (m, 2H, CH₂—CH=CH), 2.10–2.33 (m, 3H,

2.64 (brs, 1H, OH), 2.72 (t, 1H, J=3.5Hz,

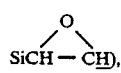

3.67 (m, 1H, CHOH), 5.40 (m, 2H).
IR (neat) 3420, 2850, 1243, 840 (cm⁻¹).
[α]$_D^{25}$ −4.2° (C 1.13, CHCl₃).

Compound 8-(3)

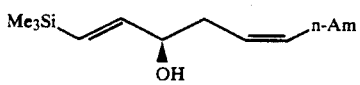

Colorless oil
¹H NMR (CCl₄, PhH): δ 0.10 (s, 9H, Si(CH₃)₃), 0.90 (t, 3H, CH₂CH₃), 1.32 (m,6H, (CH₂)₃—CH₃), 2.03 (m,2H, CH=CH—CH₂—CH₂), 2.22 (t, 2H, J=6 Hz, CH(OH)CH₂), 2,40 (brs, 1H, OH), 3 98 (dt, Jd=4 Hz, Jt=6 Hz), 5.38 (m, 2H, C—CH=CH—C), 5.74 (d, 1H, J=19 Hz, Si—CH=C), 6.02 (d=19 Hz, 4 Hz, Me₃SiC=CH—).
¹³C NMR (CDCl₃) δ 148.0, 133.3, 129.2, 124.5, 73.8, 35.1, 31.5, 29.3, 29.0, 27.4, 22,4, 13.9, 1.3.
IR (neat) 3340, 2850, 1610, 1240, 830 (cm⁻¹).
[α]$_D^{25}$ +7.6° (C 1.37, CHCl₃).

Compound 9-(2)

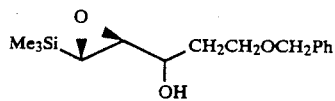

¹H NMR (CCl₄, CH₂Cl₂, D₂O): δ 0.03 (s, 9H, 3CH₃), 1.58–1.90 (m, 2H, CH₂CH₂O), 2.13 (d, J=3.6 Hz, 1H,

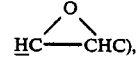

2.68 (t, J=3.6 Hz, 1 Hz,

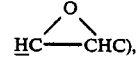

3.43–3.82 (m, 3H, CH₂O and CHO), 4.42 (s, 2H, CH₂OBn), 7.10–7.33 (m, 5H, Aromatic).
IR (neat) 3400, 1240, 1080, 835, 730, 690 (cm⁻¹).
[α]$_D^{25}$ −10.1° (C 0.97, CHCl₃).
Rf 0.23 (hexane/ether=1/1).

Compound 9-(3)

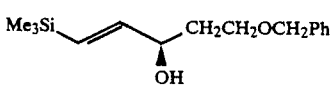

Colorless oil
¹H NMR (CCl₄, CH₂Cl₂, D₂O): δ 0.08 (s, 9H, 3CH₃), 1.60–1.90 (m, 2H, CH₂CH₂O), 3.53 (dt, J=2.5 Hz, 6.1 Hz, 2H, CH₂O), 4.04–4.26 (m, 1H, CHO), 4.42 (s, 2H, CH₂OBn), 5.80 (d, J=19.9 Hz, 1H, HC=CHC), 5.91 (dd, J=4.0 Hz, 19.9 Hz, 1H, HC=CHC), 7.08–7.30 (m, 5H, Aromatic).
IR (neat) 3380, 1090, 835, 730, 690 (cm⁻¹).
[α]$_D^{25}$ −3.2° (C 1.00, CHCl₃).
Rf 0.32 (hexane/ether=1/1).

EXAMPLE 10

The same procedure as in Example 1 was repeated except that diisopropyl L-(±)-tartrate was replaced by diisopropyl D-(−)-tartrate. The results are shown in Table 3 below.

TABLE 3

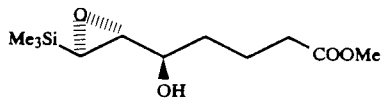

| Example No. | A | R | Reaction time (hr) | Optical purity and (yield) (2) | (3) |
|---|---|---|---|---|---|
| 10 | Me₃Si | CH₂CH₂CH₂CO₂Me | 20 | >99% ee (45%) | >99% ee (43%) |

The values of analysis are as follows:

Compound 10-(2)

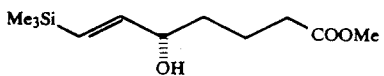

¹H NMR (CCl₄, PhH): δ 5.97 (dd, J=18.3, 3.6 Hz, 1H), 5.77 (d, J=18.3 Hz, 1H), 4.08–3.86 (m, 1H), 3.58 (s, 3H), 3.02 (brs, 1H), 2.26 (t, J=7 Hz, 2H), 2.05–1.25 (m, 4H), 0.07 (s, 9H).
¹³C NMR (CDCl₃) δ 174.0, 148.3, 129.4, 74.0, 51.4, 36.2, 33.8, 20.8, −1.4.
IR (neat) 3400, 1727, 842 (cm⁻¹).
[α]$_D^{25}$ +6.74° (C 1.75, CHCl₃).

Compound 10-(3)

Me₃Si\\\\\\\\\\\\COOMe
       OH

¹H NMR (CDCl₃, CH₂Cl₂): δ −0.08 (s, 9H), 1.2–1.8 (m, 4H), 2.08–2.29 (m, 3H), 2.62 (t, J=5.1 Hz, 1H), 2.82 (br d, J=2.4 Hz, 1H), (s, 3H), 3.40–3.62 (m, 1H).
¹³C NMR (CDCl₃) δ 173.4, 69.5, 58.1, 50.9, 47.5, 33.6, 33.0, 20.5, −4.1.
IR (neat) 3410, 1726, 1248, 843 (cm⁻¹).
[α]$_D^{25}$ +6.78° (C 1.15, CHCl₃).

EXAMPLE 11

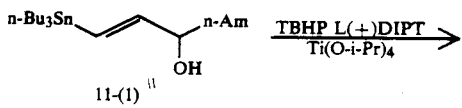

To 17 ml of CH₂Cl₂ solution (cooled to −20° C.) containing 0.72 ml of titanium tetraisopropoxide was slowly added dropwise 0.61 ml of diisopropyl L-(+)-tartrate, followed by stirring for 10 minutes. To the resulting solution was added dropwise 31 ml of CH₂Cl₂ solution containing 1.01 g of the compound 11-(1), followed by stirring for 10 minutes. Then 10.7 ml of CH₂Cl₂ solution containing 3.40M of t-butyl hydroperoxide (TBHP) was added, followed by stirring for 4 hours. After confirming by thin-layer chromatography that the ratio of 11-(2) to 11-(3) is approximately 1:1, 0.71 ml of methyl sulfide was added at −20° C., followed by stirring for 40 minutes at the same temperature. 25 ml of ethyl ether, 1 ml of 10 wt % aqueous solution of tartaric acid, 3 g of NaF, and 10 g of Celite were added at room temperature, followed by stirring for 1 hour. The resulting mixture was filtered with suction to remove precipitates, and the solvent was distilled away under reduced pressure. The resulting crude reaction product was purified by silica gel chromatography to give 433 mg of the compound 11-(3) and 450 mg of the compound 11-(2) in the oily form.

The values of analysis of the compounds 11-(2) and 11-(3) are as follows.

Compound 11-(2) Colorless oil

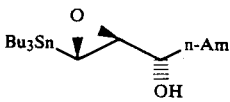

¹H NMR (Cl₄, TMS): δ 0.74–1.07 (m, 12H, 4CH₃), 1.07–1.96(m 26H, 13CH₂) 2.18 (br s, 1H, OH), 2.63–2.81 (m, 2H,

CH—CH),
 \\O/

3.59–3.81 (m, 1H, CHO).
¹³C NMR (CDCl₃): 69.6, 58.4, 48.2, 33.8, 32.0, 29.0, 27.3, 25.1, 22.5, 13.9, 13.6, 8.8.
[α]$_D^{≈}$−34.5° (C 1.10, CHCl₂, 88 %ee).
IR (neat) 3425, 2920, 2850, 1460, 1380, 1250, 1070, 1020, 862.

Compound 11-(3)

Colorless oil
¹H NMR (CCl₄, TMS): δ 0.76–1.71 (m, 39H, 4CH₃, 13CH₂, OH), 3.79–4.10 (m, 1H, CHOH), 5.54–6.40 (m, 2H, CH=CH).
[α]$_D^{≈}$−3.09° (C=1.10, CHCl₃).

EXAMPLES 12 AND 13

The same procedure as in Example 11 was repeated except that diisopropyl L-(+)-tartrate was replaced by diisopropyl-(−)-tartrate. The results are shown in Table 4 below.

TABLE 4

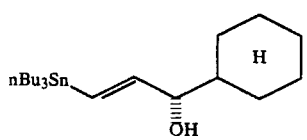

| Example No. | A | R | Reaction time (hr) | Optical purity and (yield) |
|---|---|---|---|---|
| 12 | n-Bu$_3$Sn | H (cyclohexyl) | 4 | >99% ee (41%) |
| 13 | n-Bu$_3$Sn | CH$_2$OPh | 4 | >99% ee (40%) |

The values of analysis of the compounds 12-(2) and 13-(2) are as follows.

Compound 12-(2)

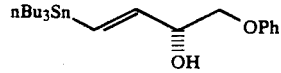

$^1$H NMR (CCl$_4$, TMS): δ 0.72-2.00 (m, 38H, 3CH$_3$, 14CH$_2$, and CH), 2.36 (brs, 1H, OH), 3.69 (t, J=4.8 Hz, 1H, CHO), 5.95 (m, 2H, HC=CH).

IR (neat): 3330, 2920, 2865, 1455, 997 (cm$^{-1}$):

Compound 13-(2)

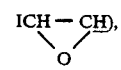

$^1$H NMR (CCl$_4$, TMS): δ 0.73-1.06 (m, 9H, 3CH$_3$), 1.08-1.99 (m, 18H, 9CH$_2$), 2.48-2.61 (m, 1H, OH), 3.72 and 3.89 (2dd, J=7.2, 9.6 Hz and 4.4, 9.6 Hz, 2H, OCH$_2$), 4.25-4.52 (m, 1H, CHO), 5.94 (dd, J=4.4, 20.4 Hz, 1H, SnCH=CH), 6.30 (d, J=20.4 Hz, 1H, SnCH), 6.71-7.27 (m, 5H, Ph).

Rf 0.45 (hexane/ether=2/1).

EXAMPLE 14

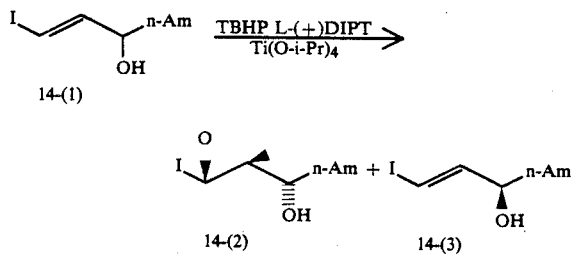

To 20 ml of CH$_2$Cl$_2$ solution (cooled to −20° C.) containing 2.33 ml of titanium tetraisopropoxide was added dropwise 1.98 ml of diisopropyl L-(+)-tartrate (DIPT) under an argon atmosphere. After stirring for 10 minutes, 7 ml of CH$_2$Cl$_2$, solution containing 1.99 g of racemic modification (dl) of 14-(1) was added dropwise, followed by stirring for minutes. Subsequently, 4.5 ml of CH$_2$Cl$_2$ solution containing 3.49M of t-butyl hydroperoxide (TBHP) was slowly added, followed by stirring at −20° C. for 3 days.

Then, 3.0 ml of methyl sulfide was added at −20° C., followed by stirring at that temperature for 40 minutes. Subsequently, 40 ml of ethyl ether 5 ml of 10 wt % aqueous solution of tartaric acid, 4 g of NaF, and 3 g of Celite were added at room temperature, followed by stirring for 30 minutes. The resulting mixture was filtered with suction to remove precipitates. After washing with 20 ml of Et$_2$O, the solvent was distilled away under reduced pressure. The values of $^1$H NMR, IR, and R$_f$ of the resulting crude product were measured for 14-(2):14-(3)=1:1. After that the crude product was purified by silica gel chromatography to obtain 758 mg of 14-(3) in the oily form. (Yield: 38%)

The values of analysis of compounds 14-(2) and 14-(3) are shown below.

Compound 14-(2)

$^1$H NMR (CCl, TMS): δ 0.70-1.06 (brt, 3H, CH$_3$), 1.06-1.85 (m, 8H, 4CH$_2$), 2.78 (brs, 1H, OH), 3.12 (dd, J=1.8, 3.0 Hz, 1H,

ICH—CH),
  \ /
   O 3.55-3.77 (m, 1H, CHOH), 4.73 (d, J=1.8 Hz, 1H,

ICH—CH).
  \ /
   O

Rf: 0.25 (hexane:ether=3:1, silica gel MERCK 5554).

IR (neat, 1:1 mixture with 14-(3)) 3340, 2930, 2860, 1605, 1400, 1260, 1170, 1020, 945 (cm$^{-1}$).

Compound 14-(3)

$^1$H NMR (CDCl$_3$). δ 0.87 (t, J=6.0 Hz, 3H), 1.06-1.76 (m, 8H), 2.45 (brs, 1H), 4.03 (q, J=6.0 Hz, 1H), 6.26 (d, J=15.6 Hz, 1H), 6.55 (dd, J=6.0, 15.6 Hz, 1H).

$^{13}$C NMR (CDCl$_3$) 13.9, 22.4, 24.7, 31.6, 36.5, 74.4, 76.8, 148.7.

IR (CCl$_4$): 3330, 1605, 940(cm$^{-1}$).

[α]$_D^{25}$ −9.9° (C=1.48, methanol).

The value of enantiomer reported in the literature (R. Noyori et al., J. Am. Chem. Soc., 106, 6717 (1984)) is as follows:

[α]$_D^{25}$ +9 87° (C=1.57, methanol).

The optical purity of 14-(3) was higher than 99.5% ee when measured by NMR after derivation to optically active ester of α-methoxy-α-trifluoromethylphenylacetic acid (Mosher ester).

EXAMPLE 15

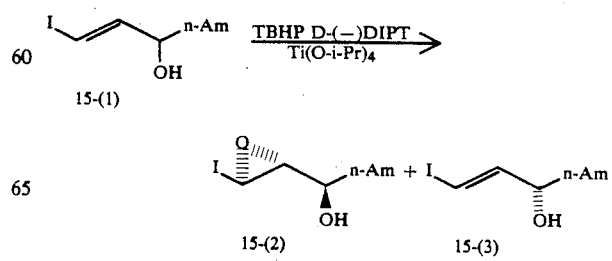

To 20 ml of CH₂Cl₂ solution (cooled to −20° C.) containing 2.33 ml of titanium tetraisopropoxide and 1.98 ml of diisopropyl D-(−)-tartrate was added dropwise 7 ml of CH₂Cl₂ solution containing 1.99 g of racemic modification (dl) of 15-(1) under an argon atmosphere. After stirring for 10 minutes, 4.5 ml of CH₂Cl₂ solution containing 3.49M of t-butyl hydroperoxide (TBHP) was slowly added, followed by stirring at −20° C. for 3 days.

Then, 3.0 ml of methyl sulfide was added at −20° C., followed by stirring at that temperature for 30 minutes. Subsequently, 5 ml of 10 wt % aqueous solution of tartaric acid, 40 ml of ethyl ether, 4 g of NaF, and 3 g of Celite were added at room temperature, followed by stirring for 30 minutes. The resulting reaction mixture was filtered with suction to remove precipitates. After washing with 20 ml of ethyl ether, the solvent was distilled away under reduced pressure. The resulting crude product was purified by silica gel chromatography to obtain 695 mg of 15-(3). (Yield: 35%).

The values of analysis of the compound 15-(3) are shown below.

Compound 15-(3)

$[\alpha]_D^{24} + 9.9°$ (C=1.48, methanol).

The NMR data, IR data, and R$_f$ values of compounds 15-(2) and 15-(3) were identical with those of compounds 14-(2) and 14-(3).

EXAMPLE 16 TO 24

The same procedure as in Example 14 was repeated. The results are shown in Table 5.

Compound 16-(2)

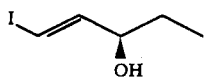

¹H-NMR (CDCl₃, TMS): δ 0.95 (t, J=7 Hz, 3H), 1.58 (dq, J=6 Hz, 7 Hz, 2H), 4.04 (brq, J=6 Hz, 1H), 6.32 (d, J=15 Hz, 1H), 6.60 (dd, J=15 Hz, 6 Hz, 1H).

MS
M⁺=212 (0.5%), [M-H₂O]=194 (5%), [CHI=CHCH₂OH]⁺=183 (14%), [C₃H₅O]⁺=57 (base peak).

$[\alpha]_D^{25} - 0.46°$ (C=1.500, MeOH).

Compound 17-(2)

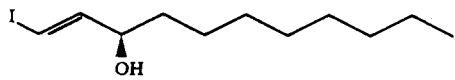

¹H-NMR (CDCl₃, TMS): δ 0.90 (t, J=5 Hz, 3H), 1.05-1.70 (m, 14H), 4.10 (q, J=6 Hz, 1H), 6.32 (d, J=15 Hz, 1H), 6.61 (dd, J=15 Hz, 6 Hz, 1H).

MS
[M-H₂O]⁺=278 (1.0%), [CHI=CHCH₂OH]⁺=183 (base peak), [C₃H₅O]⁺=57 (10%).

$[\alpha]_D^{25} - 5.98°$ (C=1.570, CHCl₃).

TABLE 5

| | | | | | | | |
|---|---|---|---|---|---|---|---|
| | | | | A⌇⌇R / OH →(TBHP (L+)-DIPT / Ti(O-iPr)₄)→ A⌇⌇R / OH | | | |
| Example No. | A | R | Reaction time (hr) | Optical purity and (yield) | | | |
| | | | | A | B | C | |
| 16 | I | Et | 19.5 | >98% ee | 98.7% ee | — | (40%) |
| 17 | I | n-C₈ | 19.5 | >98 | 99.5 | — | (45%) |
| 18 | I | cyclohexyl-CH₂ | 24 | >99 | 99.9 | — | (42%) |
| 19 | I | cyclopentyl | 46 | >99 | — | — | (44%) |
| 20 | I | Ph | 19 | >98 | 98.6 | — | (43%) |
| 21 | I | PhOCH₂ | 39 | >99 | 99.4 | — | (29%) |
| 22 | I | n-Am | 20 | >99 | 99.9 | — | (45%) |
| 23 | I | CH₂CH₂iPr | 43 | — | 98.3 | — | (39%) |
| 24 | I | CH₂CH(CH₃)(CH₂)₂CH=C(CH₃)₂ (S—) | 24 | — | — | >95 | (40%) |

A: Optical purity (A) is determined by measuring NMR of Mosher ester.
B: Optical purity (B) is determined by optical resolution high performance liquid chromatography (Sumipex OA-4100), after converting into corresponding 3,5-dinitrophenyl carbamate.
C: Optical purity (C) is determined by thin-layer chromatography (TLC).

The values of analysis of the compounds 16-(2) to 20(2) are shown below.

Compound 18-(2)

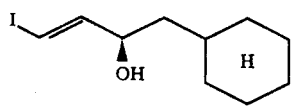

$^1$H-NMR (CDCl$_3$, TMS): δ 0.7–2.0 (m, 13H), 4.20 (q, J=6Hz, 1H), 6.32 (d, J=15 Hz, 1H), 6.60 (dd, J=15 Hz, 6 Hz, 1H).
MS
[M-H$_2$O]$^+$=262 (1%), [CHI=CHCH$_2$OH]$^+$=183 (12%), =55 (base peak).
[α]$_D^{25}$ −16 24° (C=1.557, MeOH).

Compound 19-(2)

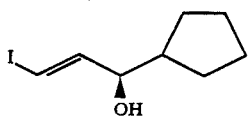

$^1$H-NMR (CDCl$_3$, TMS): δ 1.0–2.2 (m, 9H), 3.90 (t, J=6 Hz, 1), 6.33 (d, J=16 Hz, 1H), 6.63 (dd, J=16 Hz, 6 Hz, 1H).
MS
[M-H$_2$O]$^+$=234 (1%), [CHI=CHCH$_2$OH]$^+$=183 (14%), [C$_3$H$_5$O]$^+$=57 (base peak).
[α]$_D^{25}$ −12 23° (C=1.496, MeOH).

Compound 20-(2)

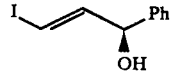

$^1$H-NMR (CDCl$_3$, TMS): δ 2.34 (brs, 1H) 5.12 (d, J=6 Hz, 1H), 6.37 (d, J=15 Hz, 1H), 6.70 (dd, J=15 Hz, 6 Hz, 1H), 6.1–6.5 (m, 5H).
[α]$_D^{25}$ −51° (C=1.018, MeOH).

Compound 21-(2)

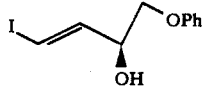

$^1$H-NMR (CDCl$_3$, TMS): δ 2.67 (d, J=4 Hz, 1H), 3.7–4.0 (m, 2H), 4.48 (dt, J=6 Hz, 4 Hz, 1H), 6.4–7.5 (m, 7H).
IR (neat) 3400, 3080, 3050, 1600, 1590, 1500, 1080, 1050, 950, 760, 700 (cm$^{-1}$).
$^{13}$C NMR (CDCl$_3$): 158.2, 143.7, 129.5, 121.3, 114.7, 79.8, 72.5, 70.6.
[α]$_D^{25}$ −10.23° (C=1.563, MeOH).

Furthermore, the properties of the compound 22-(2) are the same as those of the compound 14-(2).

Compound 23-(2)

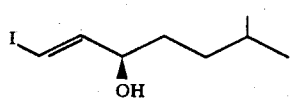

$^1$H-NMR (CDCl$_3$): δ: 0.93 (d, J=7 Hz, 6H), 1.1–2.0 (m, 6H), 4.17 (broad q, J=6 Hz, 1H), 6.37 (d, J=14 Hz, 1H), 6.55 (dd, J=14 Hz, 6 Hz, 1H).
[α]$_D^{25}$ −2.98° (C=1.574, MeOH).

Compound 24-(2)

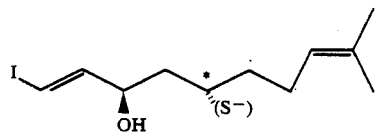

$^1$H-NMR (CDCl$_3$): δ 0.94 (d, J=6 Hz, 3H) 1.0–2.0 (m, 6H) 1.63 (s, 3H) 1.70 (s, 3H) 1.98 (q, J=7 Hz, 2H) 4.18 (broad q, J=6 Hz, 1H) 5.09 (t-like m, J=7 Hz, 1H) 6.33 (d, J=15 Hz, 1H) 6.56 (ddd, J=2,6,15 Hz, 1H).

EXAMPLES 25 TO 33

The same procedure as in Examples 16, 17, 18, 20, and 22 was repeated. The reaction time was extended as shown in Table 6 below, and the reaction ratio was traced by using 90 MHz H-NMR. The results are shown in Table 6. It is noted that the epoxidizing reaction stops mostly at 50–52% although 1.0 equivalent of t-butyl hydroperoxide (TBHP) still remains. This indicates that the reaction rate greatly differs from one enantiomer to the other.

TABLE 6

A = I $$\underset{\underset{OH}{(1)}}{A\diagdown\diagup\diagdown R} \xrightarrow[\substack{1.5 \text{ eq TBHP} \\ -20° \text{ C. Ti(O-i-Pr)}_4}]{(L+)-DIPT} \underset{\underset{OH}{(2)}}{A\diagdown\diagup\diagdown R} + \underset{\underset{O\ \ OH}{(3)}}{A\diagdown\triangle\diagdown R}$$

R    Reaction time(hr)

Reaction ratio $\frac{(3)}{(1)+(2)+(3)} \times 100$ (%)

|  | Example 16 | Example 25 | Example 26 | Example 27 |
|---|---|---|---|---|
| Et | 19.5 hr 50% | 26 hr 50% | 30 hr 50% | 45 hr 50% |
|  | Example 28 | Example 17 | Example 29 |  |
| n-C. | 14.0 hr 49% | 19.5 hr 50% | 38 hr 51% |  |
|  | Example 30 | Example 18 | Example 31 |  |
| cyclohexyl | 19.5 hr 46% | 24 hr 50% | 42.5 hr 50% |  |
|  | Example 20 | Example 32 |  |  |
| Ph | 19 hr 51% | 37 hr 52% |  |  |
|  | Example 22 | Example 33 |  |  |
| n-C$_5$ | 20 hr 52% | 27.5 hr 52% |  |  |

EXAMPLES 34 TO 38

The same procedure as in Example 14 was repeated except that the amount of t-butyl hydroperoxide was changed to 0.6–1.0 equivalent based on the substrate and the reaction temperature was changed to 0°–25° C. The results are shown in Table 7.

TABLE 7

I—CH=CH—CH(OH)—n-Am  $\xrightarrow{\text{TBHP (L+)-DIPT}}{\text{Ti(O-i-Pr)}_4}$ (1)

I—CH=CH—CH(OH)—n-Am (2)

| Example | Reaction temp. | TBHP | Reaction time | Yield | Optical purity |
|---------|---------------|--------|---------------|-------|----------------|
| 34 | 0° C. | 0.6 eq | 16 hr | 40% | 98.8% ee |
| 35 | 0° C. | 1.0 eq | 12 hr | 39 | 98.4 |
| 36 | 20° C. | 0.6 eq | 18 hr | 45 | 98.0 |
| 37 | 20° C. | 1.0 eq | 12 hr | 31 | 98.7 |
| 38 | 25° C. | 0.6 eq | 14.5 hr | 46 | 96.2 |

It is noted that the reaction can be performed at room temperature if the substrate of the invention is used, although the ordinary reaction temperature is −25° C. to −20° C.

EXAMPLE 39

In this example, an optically active allyl alcohol was epoxidized by using a catalytic amount of tartaric diester.

Me₃Si—CH=CH—CH(OH)—CH₂CH₂—CH=CH—n-Am  $\xrightarrow{\text{TBHP D(−)-DIPT}}{\text{Ti(O-i-Pr)}_4}$ 8-(3)

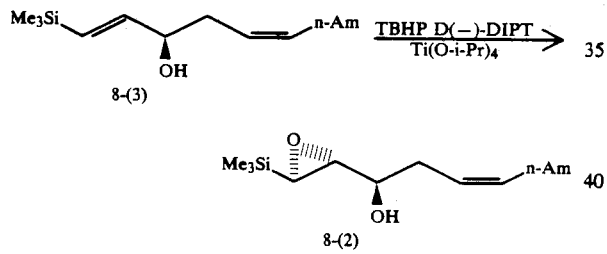

8-(2)

To 1.2 ml (5.7 mmol) of diisopropyl-(D)-(−)-tartrate cooled to −20° C. were added 1 g of powdered 3A molecular sieve, 15 ml of CH₂Cl₂, and 1.4 ml (4.7 mmol) of titanium tetraisopropoxide in an Ar atmosphere, followed by stirring for 10 minutes. 8 ml of CH₂Cl₂ solution containing 3.65 g (15.2 mmol) of 8-(3) was added. The resulting mixture was cooled to −40° C., and 7.5 ml (30.6 mmol) of t-butyl hydroperoxide (TBH) (4.09M/CH₂Cl₂) was added dropwise. The resulting mixture was stirred at −21° C. for 4 hours. 4 ml of methyl sulfide and 4 ml of 10% tartaric acid aqueous solution were added, followed by Celite filtration. The solvent was distilled away under reduced pressure, and the resulting crude product was purified by silica gel chromatography (hexane/ethyl ether=10/1→3/1, 0.5% triethylamine). There was obtained 3.3 g of desired product 8-(2). (Yield: 85%)

$[\alpha]_D^{25}$ +4 25° (C=1.15, CHCl₃).

The ¹H NMR data and IR data were identical with those of compound 8-(2).

EXAMPLE 40

In this example, the reaction was carried out by using a catalytic amount of tartaric diester.

40-(1)

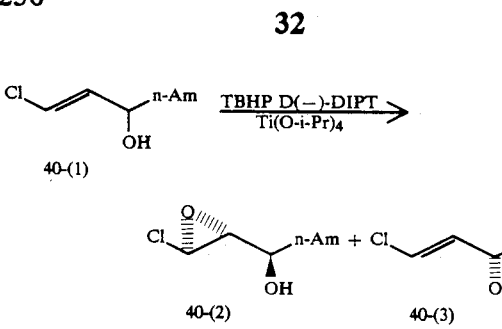

40-(2)          40-(3)

As in Example 39, the reaction was performed for 0.19 equivalent of titanium tetraisopropoxide, 0.23 equivalent of diisopropyl-(−)-tartrate, 1.0 equivalent of 40-(1), and 1.5 equivalent of t-butyl hydroperoxide at −25° C. for 35 hours. The post-treatment was carried out in the same manner as in Example 14. There was obtained compound 40-(2) (optical purity >99% ee) at a yield of 48%, and there was obtained compound 40-(3) at a yield of 48%.

The values of analysis are shown below

Compound 40-(2)

Cl—CH(O)—CH—CH(OH)—n-Am

¹H NMR (CCl₄, TMS): δ 0.90 (t, J=6.0 Hz, 3H, CH₃), 1.05–1.80 (m, 8H, 4CH₂), 2.42 (brs, 1H, OH), 3.01 (dd, J=1.2, 3.0 Hz, 1H, ClCH—CH), 3.60–3.84 (m, 1H, CHO), 4.96 (d, J=1.2 Hz, 1H, ClCH(O)).

Rf: 0.42 (hexane/ether=3/1, silica gel (MERCK 5554)).

Compound 40-(3)

Cl—CH=CH—CH(OH)—n-Am

¹H NMR (CCl₄, TMS): δ 0.90 (t, J=6.0 Hz, 3H, CH₃), 1.07–1.90 (m, 8H, 4CH₂), 2.08 (brs, 1H, OH), 3.98 (q, J=6.6 Hz, 1 Hz, CHO), 5.79 (dd, J=14.4, 6.6 Hz, 1H, ClCH=CH), 6.11 (d, J=14.4 Hz, 1H, ClCH=C).

¹³C NMR (CDCl₃): 36.3, 119.4, 71.1, 37.1, 31.6, 24.9, 22.5, 13.9.

$[\alpha]_D^{25}$ +8.1° (C 1.03, CHCl₃).

IR (neat): 3320, 2930, 2860, 1620, 1455, 1280, 1018, 933, 803 (cm⁻¹).

EXAMPLE 41

In this example, an optically active allyl alcohol was epoxidized.

Cl—CH=CH—CH(OH)—n-Am  $\xrightarrow{\text{TBHP D(−)-DIPT}}{\text{Ti(O-i-Pr)}_4}$ 40-(3)

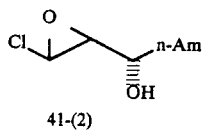

41-(2)

As in Example 39, the reaction was performed for 2 equivalent of titanium tetraisopropoxide, 2.2 equivalent of diisopropyl-(−)-tartrate, 1.0 equivalent of 40-(3), and 3 equivalent of TBHP at −25° C. for 93 hours. The yield of 41-(2) was less than 2% and almost all the raw material was recovered.

EXAMPLE 42

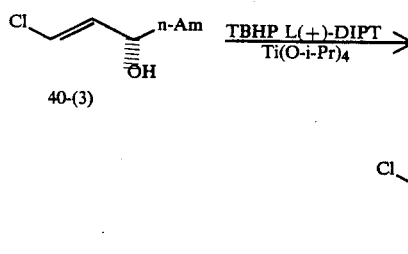

42-(2)

The reaction was carried out for 45 hours under the same conditions as in Example 41. The yield of 42-(2) was 100%.

It is noted from Examples 41 and 42 that as compared with the synthesis of the matched 42-(2) using diisopropyl(+)-tartrate, the synthesis of the mismatched 41-(2) using diisopropyl-(−)-tartrate, is so slow that the latter proceeds very little even after twice the time for the former. This suggests that the process of the invention is selective.

The values of analysis are as follows:

Compound 42-(2)

IR (neat): 3220, 2960, 2870, 1675, 1265, 915, 770 cm$^{-1}$.

Other values of analysis are identical with those of compound 40-(2).

The following Referential Examples show the process for producing the raw material compound used in Examples and the process for synthesizing various compounds from the optically active alcohols obtained in Examples.

REFERENTIAL EXAMPLE 1

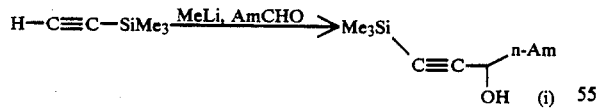

To 220 ml of ethyl ether solution (cooled to 0° C.) containing 167 mmol of methyl lithium (MeLi) was slowly added 24 g (218 mmol) of trimethyl silyl acetylene, followed by stirring at room temperature for 1 hour. The solution was cooled to −30° C. and 20.1 ml (167 mmol) of hexanal (AmCHO) was added. The solution was slowly warmed to room temperature and poured into a saturated aqueous solution of NH$_4$Cl cooled to 5° C. After separation of the organic layer, the aqueous layer was extracted twice with 100 ml portion or hexane. The extract was added to the organic layer. The organic layer was dried with MgSO$_4$ and filtered, and the solvent in the filtrate was distilled away under reduced pressure. Thus there was obtained 31.7 g (96% yield) of the compound (i).

The values of analysis of the compound (i) are as follows:

$^1$H NMR (CCl$_4$, PhH): δ 0.16 (s, 9H, 3(CH$_3$)Si), 0.92 (t, J=6.0 Hz, 3H, CH$_3$), 1.11–1.90 (m, 8H, 4CH$_2$), 2.96 (brs, 1H, OH), 4.22 (q, J=5.8 Hz, 1H, CHO).

IR (neat): 3330, 2850, 2180, 1255(cm$^{-1}$).

REFERENTIAL EXAMPLE 2

Synthesis of the compound used in Example 1-(1)

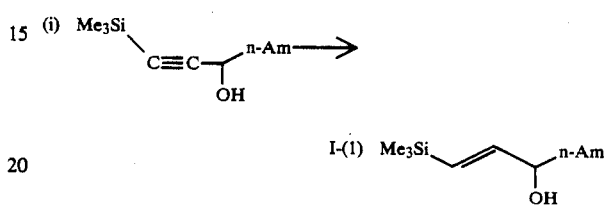

To 460 ml of ethyl ether solution (cooled to 0° C.) containing 607 mmol of i-butyl magnesium bromide (i-BuMgBr) was added 2.0 g (8 mmol) of cyclopentadienyl titanium chloride (Cp$_2$TiCl$_2$). After stirring at 0° C. for 30 minutes, 30.9 g, 156 mmol) of the compound (i) was slowly added. The solution was heated to 27° C. and stirring was continued for 7 hours at that temperature. The solution was poured into 400 ml of diluted HCl cooled to 5° C. The reaction product was extracted several times with hexane-ethyl ether mixture (1/1). The organic layer was dried with MgSO$_4$ and filtered, and the solvent in the filtrate was distilled away under reduced pressure. The crude product was purified by silica gel chromatography. Thus there was obtained 29.96 g (96% yield) of the compound 1-(1).

The values of analysis of the compound 1-(1) are as follows:

$^1$H NMR (CCl$_4$, PhH, D$_2$O): δ 0.07 (s, 9H, 3(CH$_3$)Si), 0.94 (t, J=6.0 Hz, 3H, CH$_3$), 1.10–1.75 (m, 8H, 4CH$_2$), 3.93 (q, J=4.8 Hz, 1H, CHO), 5.67 (d, J=18.0 Hz, 1H, SiOH), 6.00 (dd, J=4.8. 18.0 Hz, 1H, CH=CHSi).

$^{13}$C NMR (CDCl$_3$): −1.3, 13.9, 22.5, $\overline{25}$.0, 31.8, 36.9, 74.6, 128.8, 148.9.

IR (neat): 3330, 2930, 1645, 1285 cm$^{-1}$.

b.p.: 90° C./3 mmHg.

REFERENTIAL EXAMPLE 3

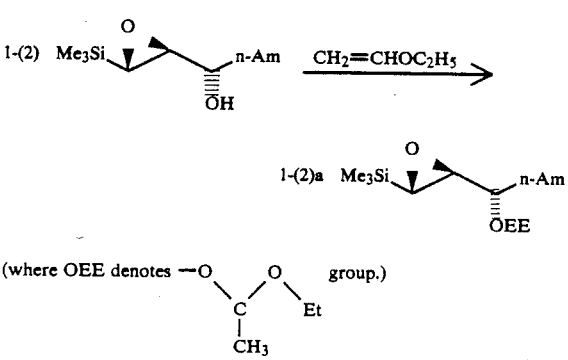

(where OEE denotes —O-C(CH$_3$)(H)-O-Et group.)

In 20 ml of dichloromethane were mixed 0.90 g (4.16 mmol) of the compound 1-(2), 1.2 ml (12.5 mmol) of ethyl vinyl ether (CH$_2$=CHOC$_2$H$_5$), and 26.8 mg of p-toluenesulfonic acid at 0° C. for 5 minutes. The reaction liquid was poured into 50 ml of saturated aqueous solution of NaHCO₃, and the aqueous layer was extracted several times with hexane. The organic layer was combined with the hexane extract. The solution was dried with MgSO₄ and then filtered. The solvent in the filtrate was distilled away under reduced pressure, and there was obtained a crude product. The crude product was purified by silica gel chromatography to obtain 1.13 g (95% yield) of the compound 1-(2)a. The values of analysis of the compound 1-(2)a are as follows:

¹H NMR (CCl₄, PhP): δ 0.03 (s, 9H, 3(CH₃)Si), 0.92 (t, J=5.0 Hz, 3H, CH₂CH₃), 1.00–1.84 (m, 14H, 2CH₃, CH₂), 2.05, 2.09 (2d, J=3.0 Hz, 1H, SiCH), 2.53, 2.58 (2dd, J=3.0, 5.0 Hz, 1H,

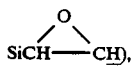, 3.03–3.75 (m, 3H, CH₂O), CHO), 4.49–4.85 (m, 1H, OCHO).

REFERENTIAL EXAMPLE 4

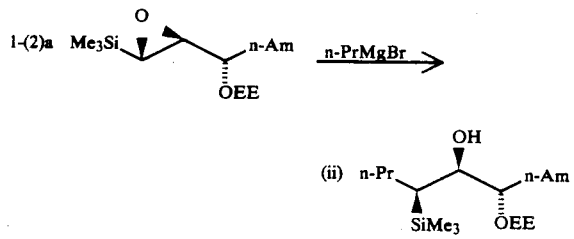

(where OEE is as defined above.)

To 25 ml of tetrahydrofuran (THF) suspension containing 98 mg of copper iodide (CuI) was added 0.7 ml of dimethyl sulfide (Me₂S) to make a uniform system. Ethyl ether solution (3 ml) of n-propyl magnesium bromide (n-PrMgBr) 3.96 m mole was slowly added at −78° C., followed by stirring for 30 minutes. Subsequently, 5 ml of THF solution containing 745 mg (2.59 mmol) of the compound 1-(2)a was added at that temperature, followed by stirring at −30° C. for 2 hours. The solution was slowly warmed to room temperature. To the solution were added 10 ml of saturated aqueous solution of NH₄Cl and 50 ml of 15% aqueous solution of NH₄OH to separate the organic layer. The organic layer was washed with 15% aqueous solution of NH₄OH and dried with MgSO₄, followed by filtration. The solvent in the filtrate was distilled away under reduced pressure to give a crude product. The crude product was purified by silica gel chromatography to obtain 756 mg (88% yield) of the compound (ii).

The values of analysis of the compound (ii) are as follows:

¹H NMR (CCl₄, PhP, D₂O): δ 0.00 (s, 9H, 3(CH₃)Si), 0.48–1.69 (m, 25H, 4CH₃, 6CH₂, CHSi), 3.19–3.86 (m, 4H, OCH₂, 2CHO), 4.40–4.80 (m, 1H, OCHO).

REFERENTIAL EXAMPLE 5

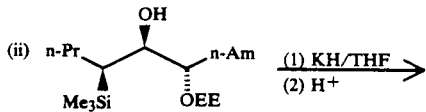

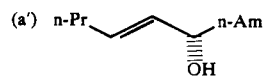

(where OEE is as defined above.)

To 10 ml of THF solution containing 120 mg of potassium hydride was slowly added dropwise 5 ml of THF solution containing 430 mg (1.30 mmol) of the compound (ii) at −72° C. The solution was slowly warmed to 5° C., and stirring was continued for 1.5 hours. To the solution were added 3 ml of saturated aqueous solution of NH₄Cl and 3 ml of dilute HCl (3N), followed by stirring at room temperature for 1 hour. The solution was extracted three times with 15 ml portion of ethyl ether. The organic layer was dried with MgSO₄ and filtered. The solvent in the filtrate was distilled away under reduced pressure to give a crude product. The crude product was purified by silica gel chromatography to obtain 205 mg (93% yield) of the compound (a'). The values of analysis of the compound (a') are as follows:

¹H NMR (CCl₄, (CH₃)₄Si): δ0.84–1.08 (m, 6H, 2CH₃), 1.10–1.74 (m, 10H, 5CH₂), 1.82–2.14 (m, 2H, CH₂CH=C), 2.40 (brs, 1H, OH), 3.72–4.05 (m, 1H, CHO), 5.17–5.69 (m, 2H, CH=CH).

¹³C NMR (CDCl₃): 13.5, 13.9, 22.3, 22.5, 25.1, 31.8, 34.2, 37.3, 73.0, 131.4, 133.4.

IR (neat): 3340, 2930, 2865, 965(cm⁻¹).

[α]$_D^{25}$: 5.1° (C 1.26, CHCl₃).

REFERENTIAL EXAMPLE 6

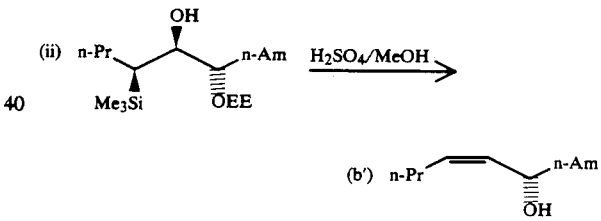

(where OEE is as defined above.)

To 5 ml of methanol solution containing 290 mg (0.87 mmol) of the compound (ii) was added 130 μl of conc. H₂SO₄ at −50° C., followed by stirring at room temperature for 2 hours. The reaction liquid was poured into 50 ml of saturated aqueous solution of NaHCO₃, and the solution was extracted three times with 15 ml portion of ethyl ether/hexane mixture (1/1). The organic layer was dried with MgSO₄ and then filtered. The solvent in the filtrate was distilled away under reduced pressure to give a crude product. The crude product was purified by silica gel chromatography to obtain 215 mg (63% yield) of the compound (b'). The values of analysis of the compound (b') are as follows:

¹H NMR (CCl₄, TMS, D₂O): δ0.72–0.12 (m, 6H, 2CH₃), 1.12–1.70 (m, 10H, 5CH₂), 1.82–2.23 (m, 2H, CH₂CH=C), 4.10–4.46 (m, 1H, CHO), 5.12–5.53 (m, 2H, CH=CH).

¹³C NMR (CDCl₃): 13.6, 13.9, 22.5, 22.8, 25.0, 29.6, 31.8, 37.5, 67.5, 131.5, 133.0.

IR (neat): 3320, 2930, 727(cm⁻¹).

[α]$_D^{25}$: −24.3° (C 0.99, CHCl₃).

REFERENTIAL EXAMPLE 7

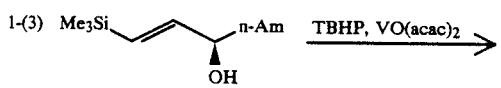

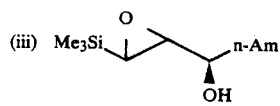

(where TBHP denotes t-butyl hydroperoxide and VO(acac)$_2$ denotes vanadyl bisacetylacetonate.)

To 30 ml of dichloromethane solution (cooled to 0° C.) containing 1.69 g (8.45 mmol) of the compound 1-(3) was added 110 mg of vanadyl bisacetylacetonate and 8.2 ml of dichloromethane solution containing 21.1 mmol of t-butyl hydroperoxide, followed by stirring overnight. 2 ml of dimethyl sulfide was added, followed by stirring for 30 minutes. The solution was poured into 30 ml of saturated aqueous solution of NaHCO$_3$, followed by stirring at room temperature for 1 hour. The solution was extracted twice with 60 ml portion of hexane/ethyl ether mixture (1/1). The organic layer was dried with Na$_2$SO$_4$ and then filtered. The solvent in the filtrate was distilled away under reduced pressure to give a crude product. The crude product was purified by silica gel chromatography to obtain 1.53 g (85% yield, anti/syn=3/1) of the compound (iii). The values of analysis of the compound (iii) are as follows:

$^1$H NMR (CCl$_4$, PhH): δ0.03 (s, 9H, 3(CH$_3$)Si), 0.85 (t, J=6 Hz, 3H, CH$_3$), 1.10–1.71 (m, 8H, 4CH$_2$), 2.05, 2.23 (2d, J=4 Hz, 1H, SiCHO), 2.69 (t, J=4 Hz, 1H,

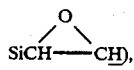

2.02–3.95 (m, 2H, CHOH).

REFERENTIAL EXAMPLE 8

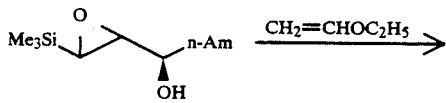

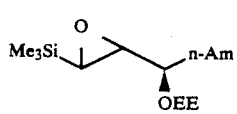

In 15 ml of dichloromethane were mixed 1.53 g (8.4 mmol) of the compound (iii), 2.4 ml of ethyl vinyl ether (CH$_2$=CHOC$_2$H$_5$), and 250 mg of pyridinium-p-toluenesulfonic acid (p-TsOH). The solution was stirred overnight. The reaction liquid was poured into 30 ml of saturated aqueous solution of NaHCO$_3$. The solution was extracted several times with hexane. The organic layer was dried with Na$_2$SO$_4$ and then filtered. The solvent in the filtrate was distilled away under reduced pressure to give 2.32 g (96% yield) of the compound (iii)a. The values of analysis of the compound (iii)a are as follows:

$^1$H NMR (CCl$_4$, PhH): δ0.05 (m, 9H, 3(CH$_3$)Si), 0.53–1.85 (m, 17H, 3CH$_3$ and 4CH$_2$), 1.86–1.94, 2.03–2.18 (2m, 1H, SiCHO), 2.48–2.78

(m, 1H SiCH——CH), 2.88–4.77 (m, 3H, OCH$_2$, CHO), 4.50–5.00 (m, 1H, OCHO).

REFERENTIAL EXAMPLE 9

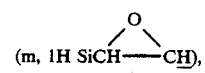

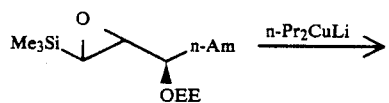

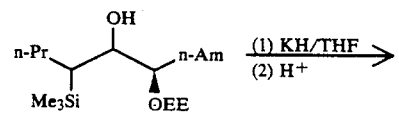

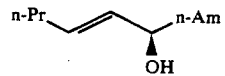

To 40 ml of ethyl ether solution containing 800 mg (4.2 mmol) of copper iodide (CuI) was slowly added dropwise at −40° C. 10.7 ml of pentane solution containing 6.96 mmol of n-propyl lithium (n-PrLi). The solution was stirred at −20° C. for 1 hour. The solution was cooled to −50° C., and 10 ml of ethyl ether solution containing 500 mg (1.7 mmol) of the compound (iii)a was added. The solution was slowly warmed to −15° C. overnight. To the reaction liquid were added 10 ml of saturated aqueous solution of NH$_4$Cl and 70 ml of 10% aqueous solution of NH$_4$OH, and the organic layer was separated. The organic layer was washed several times with 10% aqueous solution of NH$_4$OH and dried with Na$_2$SO$_4$. The solution was filtered and the solvent in the filtrate was distilled away under reduced pressure to give a crude product of the compound (iv). The crude product was subjected to the following reaction without purification.

To 10 ml of THF suspension containing 200 mg of potassium hydride was slowly added at −78° C. 5 ml of THF solution containing the compound (iv). The resulting solution was heated to 10° C. and stirred at 10° C. for 1 hour. To the solution were added 0.5 ml of saturated aqueous solution of NH$_4$Cl and 20 ml of dilute HCl (3N), followed by stirring at room temperature for 1 hour.

The reaction liquid was extracted three times with 15 ml portion of ethyl ether. The organic layer was dried with MgSO$_4$ and then filtered. The solvent in the filtrate was distilled away under reduced pressure to give a crude product. The crude product was purified by silica gel chromatography to obtain 213 mg (74% yield) of the compound (c'). The values of analysis of the compound (c') are as follows:

[α]$_D^{25}$: 4.9° (C 1.27, CHCl$_3$).

The $^1$H NMR, $^{13}$C NMR, and IR data of compound (c') are identical with those of compound (a').

REFERENTIAL EXAMPLE 10

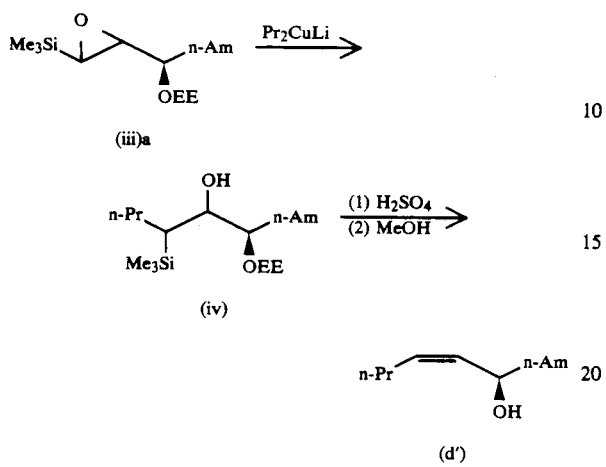

The compound (iv) was synthesized in the same manner as in Referential Example 9. That is, a crude product of the compound (iv) was prepared from 60 ml of ethyl ether solution containing 2.25 g (11.8 mmol) of copper iodide (CuI), 33 ml of ethyl ether solution containing 21.2 mg of n-propyl lithium (n-PrLi), and 1.56 g (5.4 mmol) of the compound (iii)a. 7 ml of methanol solution of the crude product of the compound (iv) was slowly added dropwise at −60° C. to 35 ml of MeOH solution containing 0.58 ml of conc. H$_2$SO$_4$. The solution was warmed to room temperature, and stirring was continued for 2.5 hours. The reaction liquid was poured into 150 ml of saturated aqueous solution of NaHCO$_3$. The resulting solution was extracted several times with hexane. The organic layer was dried with MgSO$_4$. The solvent in the filtrate was distilled away under reduced pressure to give a crude product. The crude product was purified by silica gel chromatography to obtain 390 mg (43% yield) of the compound (d'). The values of analysis of the compound (d') are as follows:

[α]$_D^{25}$: +24.9° (C 1.06, CHCl$_3$).

The $^1$H NMR, $^{13}$C NMR, and IR data of compound (d') are identical with those of compound (b').

REFERENTIAL EXAMPLE 11

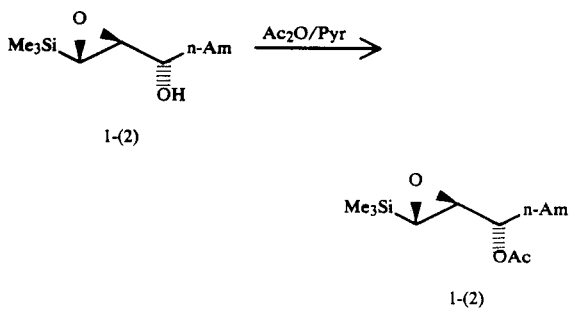

To 20 ml of pyridine solution containing 3.20 g (14.8 mmol) of the compound 1-(2) was added 4 ml (42.5 mmol) of acetic anhydride, followed by stirring at room temperature for 4 hours. The resulting solution was cooled to 0° C., and 30 ml of hexane was added 30 ml of saturated aqueous solution of NaHCO$_3$ was added slowly and stirring was continued for 15 minutes. Further, 30 ml of hexane was added for extraction. The organic layer was washed with 30 ml of water and dried with MgSO$_4$. The solution was filtered and the solvent in the filtrate was distilled away under reduced pressure to obtain a crude product. The crude product was purified by silica gel chromatography to give 3.30 g (12.8 mmol, 86% yield) of the compound 1-(2)b. The values of analysis of the compound 1-(2)b are as follows:

$^1$H NMR (CCl$_4$, PhH): δ−0.04 (s, 9H, H$_3$CSi), 0.83 (t, J=6.0 Hz, 3H, CH$_3$), 1.03–1.74 (m, 8H, CH$_2$), 1.89 (s, 3H, H,CC(=O)O), 2.02 (d, J=3.6 Hz, 1H,

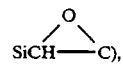

2.53 (dd, J=3.6, 6.4 Hz, 1H,

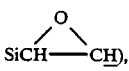

4.41 (dt, J=6.4, 6.5 Hz, 1H, OCH).
IR (neat): 1755, 1245, 860 cm$^{-1}$.

REFERENTIAL EXAMPLE 12

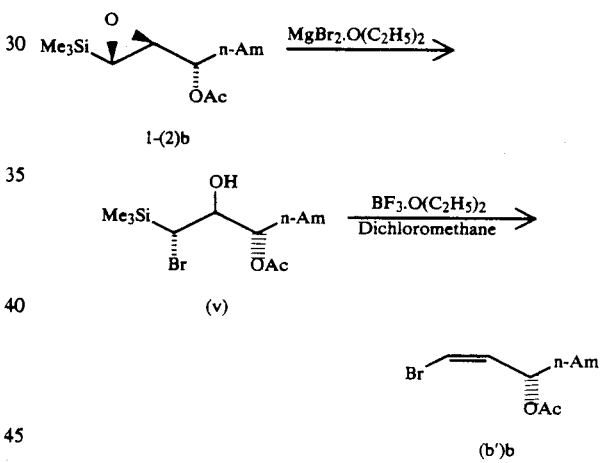

To 15 ml of diethyl ether was added 827 mg (3.20 mmol) of bromated magnesium ethylate (MgBr$_2$.O(C$_2$H$_5$)$_2$), followed by stirring at room temperature until a uniform solution was obtained. The solution was cooled to −10° C. and 5 ml of ether solution containing 413 mg (1.60 mmol) of the compound 1-(2)b was added, followed by stirring at −10° C. to −5° C. for 30 minutes. The reaction liquid was slowly added to a mixture (cooled to −1° C.) composed of 10 ml of dilute HCl (3N) and 10 ml of hexane The organic layer was dried with MgSO$_4$ and filtered. The solvent in the filtrate was distilled away under reduced pressure to obtain 514 mg of a crude product of the compound (v). The crude product as such was used for the synthesis of the compound (b')b.

To 5 ml of hexane solution containing 231 mg of the crude product of the compound (v) was added 0.285 ml (2.04 mmol) of triethanolamine and 0.1 ml (1.36 mmol) of sulfonyl chloride at 0° C. The solution was stirred for 1 hour at 0° C. The reaction liquid was added to 15 ml of saturated aqueous solution of sodium chloride. The solution was extracted with hexane, and the extract was dried with MgSO4 and filtered. The solvent in the filtrate was distilled away under reduced pressure to give a crude product of methasulfonyl ester of the compound (v).

5 ml of the THF solution of a crude compound was cooled to 0° C. and 1.55 ml of THF solution containing 1.02 ml (0.66 n in THF) of (n-Bu)4NF was added, followed by stirring at 0° C. for 15 minutes.

The reaction liquid was added to 20 ml of saturated sodium chloride aqueous solution The solution was extracted with hexane. The organic layer was dried with MgSO4 and filtered The solvent in the filtrate was distilled away under reduced pressure to obtain a crude product of the compound (b')b. The crude compounds was purified by silica gel chromatography to obtain 134 mg (79% yield calculated from the used crude compound (v)). The values of analysis of the compound (b')b are as follows: $^1$H NMR (CCl4, TMS): δ0.80 (t, J=6.0 Hz, 3H, CH3), 1.11-1.90 (m, 8H, CH2), 1.98 (s, 3H, H3CC(=O)O), 5.53 (dt, J=8.4, 6.6 Hz, 1H, OCH), 5.92-6.35 (m, 2H, CH=CH).

IR (neat): 1735, 1613, 1230 cm$^{-1}$.

REFERENTIAL EXAMPLE 13

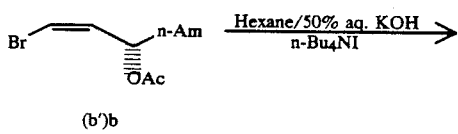

(b')b

To 25 ml of hexane solution containing 2.11 g (8.48 mmol) of the compound (b')b were added at room temperature 20 ml of 50% aqueous solution of KOH and 155 mg (0.42 mmol) of n-tetrabutyl ammonium iodide ((n-Bu)4NI), followed by stirring at 50° C. for 10 hours. After cooling to room temperature, 30 ml of water was added and the solution was extracted with 20 ml of hexane/ether mixture (1:1). The organic layer was dried with Na2SO4 and filtered. The solvent in the filtrate was distilled away under reduced pressure to obtain a crude product The crude product was purified by silica gel chromatography to give 1.05 g (8.33 mmol, 98% yield) of the compound (vi). The values of analysis of the compound (vi) are as follows:

$^1$H NMR (CCl4, (CH3)4Si, D2O): δ0.90 (t, J=6.3 Hz, 3H, CH3), 1.10-1.95 (m, 8H, CH2), 2.32 (d, J=2.3 Hz, 1H, HC C), 4.28 (dt, J=2.3, 7.0 Hz, OCH).

$^{13}$C NMR (CDCl3): δ85.2, 72.7, 62.3, 37.7, 31.4, 24.7, 22.5, 13.9.

IR (neat): 3350(s), 3300, 2120(ω), 1020 cm$^{-1}$.

b.p.: 120°-130° C./20 mmHg.

REFERENTIAL EXAMPLE 14

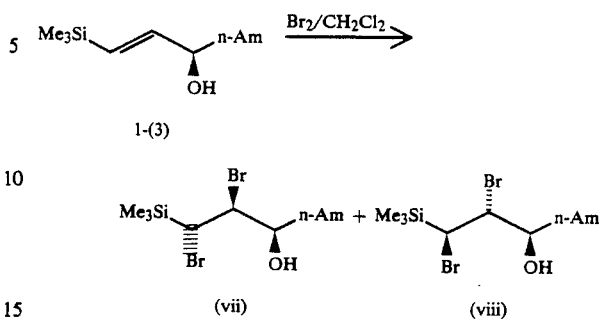

To 15 ml of dichloromethane solution (cooled to −15° C.) containing 1.77 g (8.85 mmol) of the compound 1-(3) was slowly added dropwise 0.454 ml (8.85 mmol) of Br2. Stirring was continued for 5 minutes, and 40 ml of hexane was added. The solution was washed with 15 ml of saturated aqueous solution of Na2S2O3 and then with 40 ml of water. The resulting organic layer was dried with MgSO4 and filtered. The solvent in the filtrate was distilled away under reduced pressure to give a crude product. The crude product was purified by silica gel chromatography to obtain 2.98 g (8.28 mmol, 94% yield) in total of the compounds (vii) and (viii).

REFERENCE EXAMPLE 15

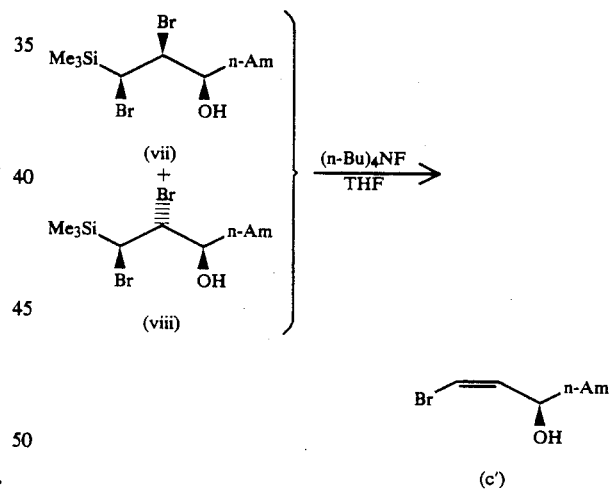

To 15 ml of THF solution (cooled to 0° C.) containing 2.97 g (8.25 mmol) in total of the compounds (vii) and (viii) was added dropwise with stirring 14.8 ml of THF solution (9.9 mmol, n=0.67) of n-tetrabutylammonium fluoride. After stirring for 5 minutes, 30 ml of water was added. The solution was extracted with 30 ml of hexane. The organic layer was dried with MgSO4 and filtered. The solvent in the filtrate was distilled away under reduced pressure to obtained a crude product of the compound (c'). The crude compound was purified by silica gel chromatography to obtain 1.55 g (7.49 mmol, 91% yield) of the compound (c'). The values of analysis of the compound (c') are as follows:

$^1$H NMR (CCl4, (CH3)4Si, D2O): δ0.90 (t, J=6.0 Hz, 3H, CH3), 1.05-1.90 (m, 8H, CH2), 4.29-4.71 (m, 1H,

OCH), 6.08 (dd, J=6.6, 7.8 Hz, 1H, BrCH=C<u>H</u>), 6.21 (d, J=6.6 Hz, 1H, BrCH=C).

IR (neat): 3350, 1620(ω) cm$^{-1}$.

$[\alpha]_D^{25}$: +40.8° (C 1.79, CHCl$_3$).

REFERENTIAL EXAMPLE 16

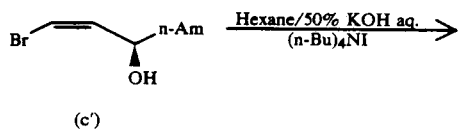

(c')

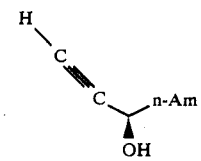

(ix)

To 20 ml of hexane solution containing 1.20 g (5.80 mmol) of the compound (c') were added at room temperature 20 ml of 50% aqueous solution of KOH and 107 mg (0.29 mmol) of n-tetrabutyl ammonium iodide, followed by stirring at 50° C. for 10 hours. After cooling to room temperature, 20 ml of water was added and the solution was extracted with 15 ml of hexane/ether mixture (1:1). The organic layer was dried with Na$_2$SO$_4$ and filtered. The solvent in the filtrate was distilled away under reduced pressure to obtain a crude product of the compound (ix). The crude product was purified by silica gel chromatography to give 727 mg (5.77 mmol, 99.5% yield) of the compound (ix). The values of analysis of the compound (ix) are as follows:

$[\alpha]_D^{25}$: +22.3° (C 1.38, ether). The $^1$H NMR, $^{13}$C NMR, and IR data of compound (ix) are identical with those of compound (vi).

The following chart shows the flow of the synthesis in Examples and Referential Examples.

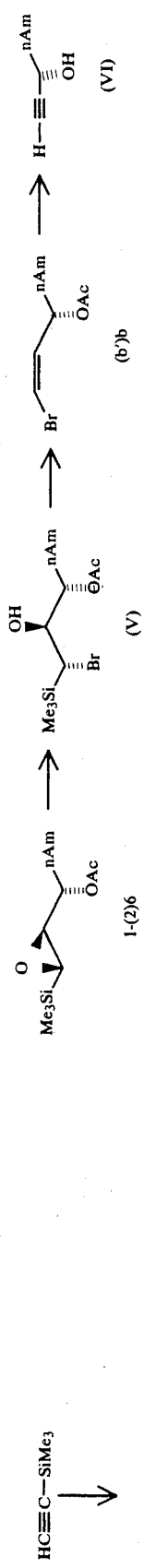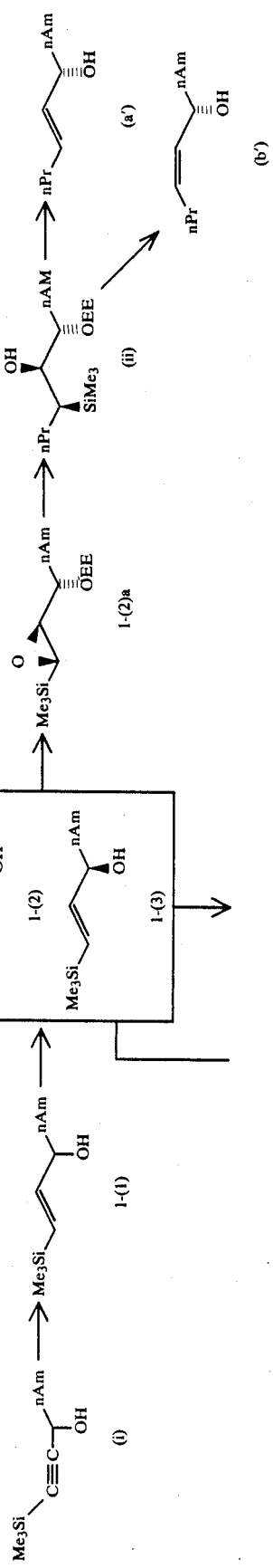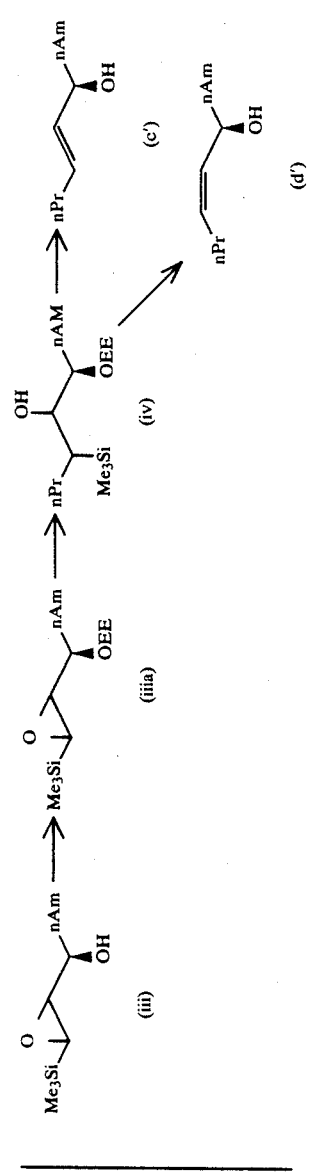

-continued
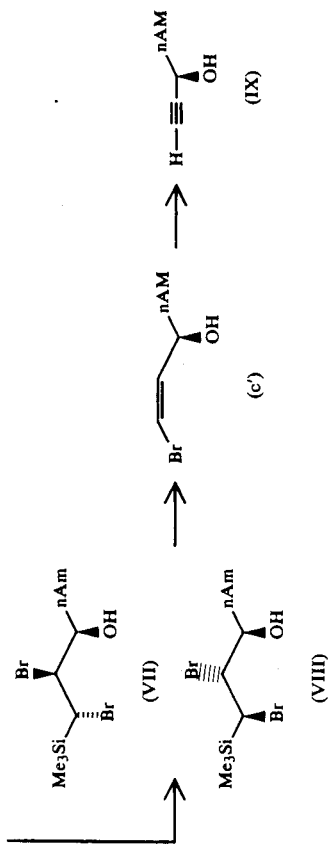

REFERENTIAL EXAMPLE 17

To 7 ml of ether solution (cooled to 0° C.) containing 543 mg of 11-(3) was added 363 m of iodine, followed by stirring at 0° C. for 1 hour. An aqueous solution of Na$_2$S$_2$O$_3$ was added. The reaction product was extracted with hexane. The extract was dried with MgSO$_4$ and condensed. The resulting oily substance was purified by silica gel chromatography to obtain 304 mg of 14-(3) in the oily form.

(Yield: 92%).

$^1$H NMR (CDCl$_3$): δ0.87 (t, J=6.0 Hz, 3H, CH$_3$), 1.06–1.76 (m, 8H, CH$_2$), 2.45 (brs, 1H, OH), 4.03 (q, J=6.0 Hz, 1H, CHO), 5.26 (d, J=15.6 Hz, 1H, HCI), 5.55 (dd, J=15.6 Hz, 6.0 Hz, 1H, IC=CH).

$[α]_D^{24}$ −9.86° (C=1.48, methanol).

This value agrees almost completely with the following value of enantiomer of 12-(3) reported in the literature. (R. Noyori et al., J. Am. Chem. Soc., 106 (1979))

$[α]_D^{24}$ 9.86° (C=1.57, methanol).

The optical purity of 14-(3) was higher than 99.5%ee when measured by NMR after derivation to optically active ester (Mosher ester) of α-methoxy-α-trifluoromethylphenylacetic acid.

REFERENTIAL EXAMPLES 18 AND 19

The same procedure as in Referential Example 17 was repeated. The results are shown in Table 8.

TABLE 8

| Referential Example No. | R | Reaction time | Optical purity and (yield) |
|---|---|---|---|
| 18 | cyclohexyl (H) | 1 hr | >99% ee (95%) |
| 19 | PhOCH$_2$ | 1 hr | >99 (90%) |

The following are the value of analysis of each compound.

The values of analysis of the compounds 18-(2) and 19-(2) are shown below.

Compound 18-(2)

$^1$H NMR (CCl$_4$, Me$_4$Si): δ0.70–2.04 (m, 11H, 5 CH$_2$ and CH), 2.86 (brs, 1H, OH), 3.72 (t, J=6.4 Hz, 1H, CHO), 6.16 (d, J=15.6 Hz, 1H, ICH=CH), 6.46 (dd, J=15.6 Hz, 6.4 Hz, CH=CHI).

$^{13}$C NMR (CDCl$_3$). δ147.6, 79.0, 77.0, 43.6, 28.8, 28.3, 26.5, 26.1.

$[α]_D^{25}$ +11.8° (C 1.17, CHCl$_3$).

IR (neat) 3320, 2910, 2850, 1605 (cm$^{-1}$).

Compound 19-(2)

$^1$H NMR (CCl$_4$, Me$_4$Si). δ3.03 (brs, 1H, OH), 3.56–3.98 (m, 2H, CH$_2$), 4.30 (dt, J=7.0, 4.0 Hz, 1H, CHO), 6.38 (d, J=16.0 Hz, 1H, ICH), 6.46–6.67 (m, 1H, IC=CH), 6.57–7.28 (m, 5H, OPh).

$[α]_D^{25}$ −8.8° (C 1.41, CHCl$_3$).

IR* (neat) 3400, 3080, 3050, 1600, 1590, 1500, 1080, 1050, 950, 760, 700 (cm$^{-1}$).

$^{13}$C NMR* (CDCl$_3$). δ158.2, 143.7, 129.5, 121.3, 114.7, 79.8, 72.5, 70.6.

What is claimed is:

1. A process for producing an optically active alcohol having a silyl group, stannyl group, or halogen atom at the γ-position, selected from compounds represented by the general formula [I], the general formula [II], the general formula [III], and the general formula [IV], (where, R denotes a C$_1$–C$_{10}$ substituted or unsubstituted alkyl group or substituted or unsubstituted phenyl group; A denotes a silyl group represented by a stannyl group represented by

or a halogen atom. $R^1$, $R^2$, and $R^3$ are substituted or unsubstituted $C_1$-$C_{10}$ alkyl groups or substituted or unsubstituted phenyl group, which may be the same or different), said process comprising oxidizing transallyl alcohol having a silyl group, stannyl group, or halogen atom at the γ-position, selected from the compounds represented by the general formula [V]

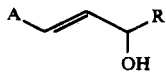  [V]

(where, R denotes a $C_1$-$C_{10}$ substituted or unsubstituted alkyl group or substituted or unsubstituted phenyl group; A denotes a silyl group represented by

a stannyl group represented by

or a halogen atom. $R^1$, $R^2$, and $R^3$ are substituted or unsubstituted $C_1$-$C_{10}$ alkyl groups or substituted or unsubstituted phenyl group, which may be the same or different) with hydroperoxide in the presence of titanium tetraalkoxide and optically active tartaric diester.

2. The process as claimed in claim 1, wherein the titanium alkoxide is one or more members selected from titanium tetraalkoxide, titanium tetraethoxide, titanium tetrapropoxide, titanium tetraisopropoxide, titanium tetrabutoxide, and titanium tetra-t-butoxide.

3. The process as claimed in claim 1, wherein the titanium tetraalkoxide is used in an amount of 0.05 to 1.5 mol for 1 mol of trans-allyl alcohol represented by the general formula [V].

4. The process as claimed in claim 1, wherein the optically active tartaric diester is one or more members selected from dimethyl L-(+)-tartrate, diethyl L-(−)-tartrate, diisopropyl L-(+)-tartrate, di-t-butyl L-(+)-tertrate, distearyl L-(+)-tartrate, diphenyl L-(+)-tartrate and D-(−)-isomers thereof.

5. The process as claimed in claim 1, wherein the optically active diester is used in an amount of 0.9–2 mol for 1 mol of the titanium tetraalkoxide.

6. The process as claimed in claim 1, wherein the hydroperoxide is one or more members selected from t-butyl hydroperoxide, α,α-dimethylheptyl hydroperoxide, bis-isobutyl-2,5-dihydroperoxide, 1-methylcyclohexyl hydroperoxide, cumene hydroperoxide, and cyclohexyl hydroperoxide.

7. The process as claimed in claim 1, wherein the hydroperoxide is used in an amount of 0.5–3 mol for 1 mol of the trans-allyl alcohol represented by the general formula [V].

8. The process as claimed in claim 1, wherein the solvent is a halogenated hydrocarbon.

* * * * *